(12) United States Patent
Lambert et al.

(10) Patent No.: US 6,667,048 B1
(45) Date of Patent: *Dec. 23, 2003

(54) EMULSION VEHICLE FOR POORLY SOLUBLE DRUGS

(75) Inventors: Karel J. Lambert, Woodinville, WA (US); Panayiotis P. Constantinides, Bothell, WA (US); Steven C. Quay, Edmonds, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/361,935

(22) Filed: Jul. 27, 1999

Related U.S. Application Data

(63) Continuation of application No. 09/003,173, filed on Jan. 5, 1998, now Pat. No. 6,458,373.
(60) Provisional application No. 60/048,840, filed on Jun. 6, 1997, and provisional application No. 60/034,188, filed on Jan. 7, 1997.

(51) Int. Cl.[7] .................................................. A61K 9/10
(52) U.S. Cl. ........................ 424/405; 514/938; 514/975
(58) Field of Search ........................... 424/486, 422–23; 514/938, 975

(56) References Cited

U.S. PATENT DOCUMENTS

| 4,439,432 A | 3/1984 | Peat ............................ 424/240 |
| 4,551,332 A | 11/1985 | Stillman |
| 4,578,391 A | 3/1986 | Kawata et al. ............... 514/256 |
| 4,784,845 A | 11/1988 | Desai et al. |
| 4,797,285 A | 1/1989 | Barenholz et al. |
| 4,898,735 A | 2/1990 | Barenholz et al. |
| 4,960,814 A | 10/1990 | Wu et al. .................... 524/312 |
| 5,002,767 A | 3/1991 | Massë |

(List continued on next page.)

FOREIGN PATENT DOCUMENTS

| AU | B-24213/88 | 2/1992 | .......... A61K/37/02 |
| AU | B-70937/91 | 9/1994 | .......... A61K/31/355 |

(List continued on next page.)

OTHER PUBLICATIONS

Alade, S. et al., *Polysorbate 80 and E–Ferol Toxicity*, Pediatrics vol. 77, No. 4 (1986).

Alkan–Onyuksel, H, et al. "A Mixed Micellar Formulation Suitable for the Parenteral Administration of Taxol", Pharmaceutical Research 2(2): 206–212 (1994).

(List continued on next page.)

*Primary Examiner*—Edward J. Webman
(74) *Attorney, Agent, or Firm*—Christensen O'Connor Johnson Kindness PLLC

(57) ABSTRACT

An emulsion of α-tocopherol, stabilized by biocompatible surfactants, as a vehicle or carrier for therapeutic drugs, which is substantially ethanol free and which can be administered to animals or humans various routes is disclosed. Also included in the emulsion is PEGylated vitamin E. PEGylated α-tocopherol includes polyethylene glycol subunits attached by a succinic acid diester at the ring hydroxyl of vitamin E and serves as a primary surfactant, stabilizer and a secondary solvent in emulsions of α-tocopherol.

21 Claims, 3 Drawing Sheets

U.S. PATENT DOCUMENTS

| | | | |
|---|---|---|---|
| 5,041,278 A | 8/1991 | Janoff et al. | |
| 5,114,957 A | 5/1992 | Hendler et al. | |
| 5,179,122 A | 1/1993 | Greene et al. | 514/458 |
| 5,330,689 A | 7/1994 | Janoff et al. | |
| 5,387,579 A | 2/1995 | Maybeck et al. | |
| 5,391,377 A | 2/1995 | Barnwell | |
| 5,407,683 A | 4/1995 | Shively | 424/439 |
| 5,478,860 A | 12/1995 | Wheeler et al. | 514/449 |
| 5,504,102 A | 4/1996 | Agharkar et al. | 514/449 |
| 5,532,002 A | 7/1996 | Story | |
| 5,534,499 A | 7/1996 | Ansell | |
| 5,573,781 A | 11/1996 | Brown et al. | |
| 5,583,105 A | 12/1996 | Kovacs et al. | |
| 5,614,549 A | 3/1997 | Greenwald et al. | |
| 5,616,330 A | 4/1997 | Kaufman et al. | 424/400 |
| 5,621,001 A | 4/1997 | Canetta et al. | 514/449 |
| 5,626,869 A | 5/1997 | Nyqvist et al. | 424/450 |
| 5,648,506 A | 7/1997 | Desai et al. | |
| 5,653,998 A | 8/1997 | Hamann et al. | |
| 5,681,846 A | 10/1997 | Trissel | |
| 5,683,715 A | 11/1997 | Boni et al. | 424/450 |
| 5,726,181 A | 3/1998 | Hausheer et al. | |
| 5,877,205 A * | 3/1999 | Andersson | |

FOREIGN PATENT DOCUMENTS

| | | | |
|---|---|---|---|
| AU | B27266/92 | 4/1995 | A61K/7/48 |
| EP | 0 001 851 | 5/1979 | A61K/9/00 |
| EP | 0 299 528 | 7/1988 | A61K/31/71 |
| EP | 0 427 582 A2 | 5/1991 | |
| EP | 0 546 951 | 12/1992 | A61K/37/02 |
| EP | 0 382 779 B1 | 8/1993 | A61K/37/20 |
| EP | 0382 779 B1 | 8/1993 | A61K/37/20 |
| EP | 0 700 679 A1 | 8/1995 | A61K/9/127 |
| EP | 0 712 631 A2 | 5/1996 | A61K/38/13 |
| EP | 0 474 647 B1 | 2/1997 | A61L/15/44 |
| EP | 0 988 858 A1 | 3/2000 | |
| WO | WO 88/06442 | 9/1988 | A61K/9/66 |
| WO | WO 89/03689 | 5/1989 | A61K/37/20 |
| WO | WO 92/13531 | 8/1992 | A61K/31/355 |
| WO | WO 94/12154 | 6/1994 | A61K/9/127 |
| WO | WO 94/20143 | 9/1994 | A61K/47/02 |
| WO | WO 95/01785 | 1/1995 | A61K/9/48 |
| WO | WO 95/11039 | 4/1995 | A61K/38/13 |
| WO | WO 95/20943 | 8/1995 | A61K/9/127 |
| WO | WO 95/24892 | 9/1995 | A61K/9/12 |
| WO | WO 95/25504 | 9/1995 | A61K/9/107 |
| WO | WO 95/31217 | 11/1995 | A61K/47/22 |
| WO | WO 96/15774 | 5/1996 | A61K/9/127 |
| WO | WO 96/17593 | 6/1996 | A61K/9/107 |
| WO | WO 96/17594 | 6/1996 | A61K/9/107 |
| WO | WO 96/17899 | 6/1996 | C09K/15/04 |
| WO | WO 96/22103 A1 | 7/1996 | |
| WO | WO 96/32094 | 10/1996 | A61K/9/127 |
| WO | WO 96/33697 | 10/1996 | A61K/9/107 |
| WO | WO 96/33987 | 10/1996 | C07D/311/72 |
| WO | WO 96/40056 | 12/1996 | A61K/9/107 |
| WO | WO 97/03651 | 2/1997 | A61K/9/107 |
| WO | WO 97/07113 | 2/1997 | C07D/311/72 |
| WO | WO 97/09964 | 3/1997 | A61K/9/107 |
| WO | WO 97/10849 | 3/1997 | A61K/47/34 |
| WO | WO 97/11682 | 4/1997 | A61K/9/107 |
| WO | WO 97/13528 | 4/1997 | A61K/47/14 |
| WO | WO 97/14705 | 4/1997 | C07F/9/655 |
| WO | WO 97/22358 | 6/1997 | A61K/38/13 |
| WO | WO 97/23192 | 7/1997 | A61K/7/00 |
| WO | WO 97/28151 | 8/1997 | C97D/311/72 |
| WO | WO 97/30695 | 8/1997 | A61K/9/107 |
| WO | WO 97/29773 | 9/1997 | A61K/39/39 |
| WO | WO 97/33552 | 9/1997 | A61K/5/00 |
| WO | WO 97/36611 | 10/1997 | A61K/38/13 |
| WO | WO 97/44124 | 11/1997 | B01J/13/00 |
| WO | WO 97/46204 | 12/1997 | |
| WO | WO 98/00110 | 1/1998 | A61K/9/107 |
| WO | WO 98/00128 | 1/1998 | A61K/31/335 |
| WO | WO 98/08597 | 3/1998 | B01F/17/34 |
| WO | WO 98/11902 | 3/1998 | A61K/31/71 |
| WO | WO 98/18321 | 5/1998 | A01N/25/30 |
| WO | WO 98/21197 | 5/1998 | C07D/311/00 |
| WO | WO 98/30204 A1 | 7/1998 | |
| WO | WO 98/30204 | 7/1998 | A61K/9/107 |
| WO | WO 98/30205 A1 | 7/1998 | |
| WO | WO 98/37869 | 9/1998 | A61K/9/107 |
| WO | WO 98/40051 | 9/1998 | A61K/9/107 |
| WO | WO 98/40094 | 9/1998 | A61K/38/13 |

OTHER PUBLICATIONS

Arrowsmith, J. et al., *Morbidity and Mortality Among Low Birth Weight Infants Exposed to an Intravenous Vitamin E Product, E–Ferol*, Pediatrics, vol. 873, No. 2 (1989).

Balistreri, W. et al., *Lesions from the E–Ferol Tragedy*, Pediatrics vol. 78, No. 3 (1986).

Bateman N.E., et al., "*Kinetics of D–α–tocopherol in a water soluble base in man*" J. Pharm. Pharmacol. 37:728–729 (1985).

Bignami, G. et al., *Biological Activity of 26–succinylbryostatin 1*, Biochimica et Biohphysica Acta 1312 pp. 197–206, (1996).

Brunzell, J. D., et al., "*Pathophysiology of Lipoprotein Transport*", Metabolism 27(9): 1109–1127 (1976).

Cherng–Chyi Fu, R., et al., "*The Biocompatibility of Parenteral Vehicles—In Vitro/In Vivo Screening Comparison and the Effect of Excepients on Hemolysis*", J. Parenter. Sc. Tech., 41(5): 164–168 (1987).

Chun Li, et al; *Complete Regression of Well–established Rumors Using a Novel Water–Soluble Poly(1–Glutamic Acid) –Paclitaxel Conjugate*, Cancer Research 58, pp. 2404–2409, (1998).

Constantinides, P., *Lipid Microemulsions for Improving Drug Dissolution and Oral Absorption: Physical and Biopharmaceutical Aspects*, Pharmaceutical Research, vol. 12, No. 11 (1995).

Coon, J. et al., *Solutol HS 15, Nontoxic Polyoxyethylene Esters of 12–Hydroxystearic Acid, Reversis Multidrug Resistance*, Cancer Research 51, pp. 897–902 (1991).

Dasgupta, J., et al., *Vitamin E, Its Status and Role in Leukemia and Lymphoma*, Neoplasma, vol. 40, No. 4 (1993).

Davis, S., et al., *Lipid Emulsions as Drug Delivery Systems*, Annals New York Academy of Sciences, pp. 75–84.

Eastman Vitamin E TPGS, "*Products and Applications*", Eastman Chemical Company Publication EFC–226 (1996).

Farah, N., et al., *Self–Microemulsifying Drug Delivery Systems for Improving In–Vitro Dissolution of Drugs*, Gattefosse s.a. PF 9386, No. 173.

Fariss, M., et al., *The Selective Antiproliferative Effects of α–Tocopheryl Hemisuccinate and Cholesteryl hemisuccinate on Murine Leukemia Cells Result from the Action of the Intact Compounds*, Cancer Research 54, pp. 3346–3351, (1994).

Geetha, A., et al., *α–Tocopherol Reduces Doxorubicin–Induced Toxicity in Rates—Histological and Biochemical Evidences*, Ind. J. Physiol. Pharmac, 34(2), pp. 94–100 (1990).

Hadfield, J.I.H., "Preoperative and Postoperative Intravenous Fat Therapy", Hadfield: Intravenous Fat Therapy, Brit. J. Surg. 52(4):291–298 (1965).

Hansrani, P.K., et al, "The Preparation and Properties of Sterile Intravenous Emulsions" J. Parenter. Sc. Tech. 37:145–150 (1983).

Heird, W. C., et al., "Total parenteral nutrition", Medical Progress, J. of Pediatrics 86(2):2–16 (1975).

Hidiroglou, M., et al., "Pharmacokinetic disposition in sheep of various vitamin E preparations given orally or intravenously", British J. of Nutrition, 59:509–518 (1988).

Ingold, K. U., et al., Autoxidation of lipids and antioxidation by α–tocopherol and ubiquinol in homogeneous solution and in aqueous dispersions of lipids: Unrecognized consdquences of lipid particle size as exemplified by oxidation of human low density lipoprotein, Proc. Natl. Acad. Sci. USA, 90:45–49 (1993).

Israel, K., et al., RRR–α–Tocopheryl Succinate Inhibits the Proliferation of Human Prostatic Tumor Cells with Defective Cell Cycle/Differentiation Pathways, Lawrence Erlbaum Assoicates, Inc., vol. 24, No. 2, (1995).

Kagkadis, K. A., et al., "A Freeze–Dried Injectable Form of Ibuprofen: Development and Optimisation Using Response Surface Methodology", 560(5):317 (1996).

Kato, Y., et al., Blood Clearance and tissue Distribution of Various Formulations of α–Tocopherol Injection After Intravenous Administration, Chem. Pharm. Bull. 41(3) pp. 599–605 (1993).

Kelloff et al., "Clinical Development Plan: Vitamin E", J. Cellular Biochem. Suppl. 20:282–299.

Kleinerman, E. et al., Activation of Tumoricidal Properties in Human Blood Monocytes by Liposomes Containing Lipophilic Muramyl Tripeptide, Cancer Research, vol. 43, pp. 2010–2014, (1983).

Klostergaard, J., Macrophage Tumoricidal Mechanisms, 50th Forum in Immunology.

Kurihara, A., et al., Enhanced Tumor Delivery and Antitumor Activity of Palmitoyl Rhizoxin Using Stable Lipid Emulsions in Mice, Pharmaceutical Reserach, vol. 13, No. 2 (1996).

Lidgate, D., et al., Sterile Filtration of a Parenteral Emulsion, Pharmaceutical Research, vol. 9, No. 7, (1992).

Lundberg, B., A Submicron Lipid Emulsion Coated with Amphipathic Polyethylene Glycol for Parenterial Administration of Paclitaxel (Taxol), J. Pharm. Pharmacol. vol. 49, pp. 116–121 (1997).

Lundberg, B., Preparation of Drug–Carrier Emulsions Stabilized with Phosphatidylcholine–Surfactant Mixtures, Journal of Pharmaceutical Sciences, vol., 83, No. 1, (1994).

Matilla, M.A.K., et al., "Intravenous premedication with diazepan", Anaesthesis, 39:879–882 (1984).

Meng, H.C., "Use of Fat Emulsions in Parenteral Nutrition", I.V. Additive Review, Drug Intelligence and Clinical Pharm. 6:321–330 (1972).

Microemulsions: Formulation Guide, Gattefossè, PF 9225A (1994).

Myers, S., et al., Preparation and Characterization of Emulsifiable Glasses: Oil–in–Water and Water–in–Oil–Water Emulsions, Journal of Colloid and Interface Science, vol. 149, No. 1, (1992).

Nakamoto, Y., et al., Studies on Pharmaceutical Modification of Anticancer Agents. Enhancement of Lymphatic Transport of Mitomycin C by Parenterial Emulsions, Chem. Pharm. Bull. vol. 23, No. 10 pp. 2232–2238 (1975).

Ojima, I, et al., Syntheses and Structure–Activity Relationships of the Second–Generation Antitumor Taxoids: Exceptional Activity Against Drug–Resistant Cancer Cells, J. Med. Chem. vol. 39, pp. 3889–3896 (1996).

Prankerd, R.J., et al., "Preliminary Development and Evaluation of a parenteral Emulsion Formulation of Penclomedine (NSC–338720;3, 5–dichloro–2, 4–dimethoxy–6–trichloromethylpyridine): A novel, Practically Water Insoluble Cytotoxic Agent", J. Parenter. Sc. Tech. 42:76–81 (1988).

Prankerd, R.J., et al., "The Use of Oil–in–Water Emulsions as a Vehicle for Parenteral Drug Administration", J. Parenter. Sc. Tech., 44:139–149 (1990).

Prasad, K., et al., Modification of the Effect of Tamoxifen, cis–Platin, DTIC, and Interferon–α2b on Human Malanoma Cells in Culture by a Mixture of Vitamins, Lawrence Erlbaum Associates, Inc., vol. 24, No. 3, pp. 233–245, (1994).

Remington's Pharmaceutical Sciences, Fifteenth Edition, (1975).

Saladino, C., et al., Platelet Aggregability in Rats with Early Atheroslerotic Changes Induced by Parenterally–Administered Lipid Emulsions, Atherosclerosis, vol. 66, pp. 19–28 (1987).

Simamora, P., et al: Emulsion Formulations for Intravenous Administration of Paclitaxela Journal of Pharmaceutical Science & Technology, vol. 52, No. 4, (1998).

Singh, M. et al., "Parenteral Emulsions as Drug Carrier Systems", J. Parenter Sci. Tech., 40:34–41 (1990).

Sweetana, S., et al., "Solubility Principles and practices for Parenteral Drug Dosage Form Development", PDA J. Pharm. Sc. Tech., 50:(5):330–342 (1996).

Takahashi, T., et al., Enhancement of the Cancer Chemotherapeutic Effect by Anticancer Agents in the Form of Fat Emulsion, Tohoku J. Exp. Med. vol. 123, pp.215–246 (1977).

Takeuchi, H., et al., Redispersible Dry Emulsion System as Novel Oral Dosage Form of Oily Drugs: In Vivo Studies in Beagle Dogs, Chem. Pharm. Bull. No. 39, vol. 12, pp. 3362–3364 (1991).

Takeuchi, H., et al., Preparation of Powdered Redispersible Vitamin E Acetate Emulsions by Spray–Drying Technique, Chem. Pharm. Bull. vol. 39, No. 6, pp. 1528–1531 (1994).

Tarr, B., et al., A New Parenterial Emulsion for the Administration of Taxol, Pharmaceutical Research, vol. 4, No. 2 (1987).

Tengerdy R. P., et al., "Vitamin E adjuvant formulation in mice".

Urano, S., et al., Vitamin E: Inhibition of Retinol–Induced Hemolysis and Membrane–Stabilizing Behavior, Journal of Biological Chemistry, vol. 267, No. 26, pp. 18365–18370 (1992).

Wadleigh, R., et al., Vitamin E in the Treatment of Chemotherapy–Induced Mucositis, Americna Journal of Medicine, vol. 92, pp. 481–484 (1992).

Wheeler, J.J., et al., "Polyethylene Glycol Modified Phospholipids Stabilize Emulsions Prepared from Triacylglycerol", J. Pharm. Sciences, 83(11):1558–1564 (1994).

Yao, T., et al., "Inhibition of carbon tetrachloride–induced liver injury by liposomes containing vitamin E", Am Physiological Soc. G476–484 (1994).

* cited by examiner

EMULSION VEHICLE FOR POORLY SOLUBLE DRUGS

CROSS-REFERENCES TO RELATED APPLICATIONS

This application is a continuation of U.S. Patent application No. 09/003,173, filed Jan. 5, 1998, now U.S. Pat. No. 6,458,373, which claims the benefit of U.S. Provisional Application No. 60/048,840, filed Jun. 6, 1997, and U.S. Provisional Application No. 60/034,188, filed Jan. 7, 1997.

BACKGROUND OF THE INVENTION

Hundreds of medically useful compounds are discovered each year, but clinical use of these drugs is possible only if a drug delivery vehicle is developed to transport them to their therapeutic target in the human body. This problem is particularly critical for drugs requiring intravenous injection in order to reach their therapeutic target or dosage but which are water insoluble or poorly water soluble. For such hydrophobic compounds, direct injection may be impossible or highly dangerous, and can result in hemolysis, phlebitis, hypersensitivity, organ failure and/or death. Such compounds are termed by pharmacists "lipophilic", "hydrophobic", or in their most difficult form, "aamphiphobic".

A few examples of therapeutic substances in these categories are ibuprofen, diazepam, griseofulvin, cyclosporin, cortisone, proleukin, etoposide and paclitaxel. Kagkadis, KA et al. (1996) PDA J Pharm Sci Tech 50(5):317–323; Dardel, O. 1976. Anaesth Scand 020:221–24. Sweetana, S and MJU Akers. (1996) PDA J Pharm Sci Tech 50(5) :330–342.

Administration of chemotherapeutic or anti-cancer agents is particularly problematic. Low solubility anti-cancer agents are difficult to solubilize and supply at therapeutically useful levels. On the other hand, water-soluble anti-cancer agents are generally taken up by both cancer and non-cancer cells thereby exhibiting non-specificity.

Efforts to improve water-solubility and comfort of administration of such agents have not solved, and may have worsened, the two fundamental problems of cancer chemotherapy: 1) non-specific toxicity and 2) rapid clearance form the bloodstream by non-specific mechanisms. In the case of cytotoxins, which form the majority of currently available chemotherapies, these two problems are clearly related. Whenever the therapeutic is taken up by noncancerous cells, a diminished amount of the drug remains available to treat the cancer, and more importantly, the normal cell ingesting the drug is killed.

To be effective in treating cancer, the chemotherapeutic must be present throughout the affected tissue(s) at high concentration for a sustained period of time so that it may be taken up by the cancer cells, but not at so high a concentration that normal cells are injured beyond repair. Obviously, water soluble molecules can be administered in this way, but only by slow, continuous infusion and monitoring, aspects which entail great difficulty, expense and inconvenience.

A more effective method of administering a cancer therapeutic, particularly a cytotoxin, is in the form of a dispersion of oil in which the drug is dissolved. These oily particles are made electrically neutral and coated in such a way that they do not interact with plasma proteins and are not trapped by the reticuloendothelial system (RES), instead remaining intact in the tissue or blood for hours, days or even weeks. In most cases, it is desirable if the particles also distribute themselves into the surrounding lymph nodes which are injected at the site of a cancer. Nakamoto, Y et al. (1975) Chem Pharm Bull 23(10):2232–2238. Takahashi, T et al. (1977) Tohoku J Exp Med 123:235–246. In many cases direct injection into blood is the route of choice for administration. Even more preferable, following intravenous injection, the blood-borne particles may be preferentially captured and ingested by the cancer cells themselves. An added advantage of a particulate emulsion for the delivery of a chemotherapeutic is the widespread property of surfactants used in emulsions to overcome multidrug resistance.

For drugs that cannot be formulated as an aqueous solution, emulsions have typically been most cost-effective and gentle to administer, although there have been serious problems with making them sterile and endotoxin free so that they may be administered by intravenous injection. The oils typically used for pharmaceutical emulsions include saponifiable oils from the family of triglycerides, for example, soybean oil, sesame seed oil, cottonseed oil, safflower oil and the like. Hansrani, PK et al., (1983) J Parenter Sci Technol 37:145–150. One or more surfactants are used to stabilize the emulsion, and excipients are added to render the emulsion more biocompatible, stable and less toxic. Lecithin from egg yolks or soybeans is a commonly used surfactant. Sterile manufacturing can be accomplished by absolute sterilization of all the components before manufacture, followed by absolutely aseptic technique in all stages of manufacture. However, improved ease of manufacture and assurance of sterility is obtained by terminal sterilization following sanitary manufacture, either by heat or by filtration. Unfortunately, not all emulsions are suitable for heat or filtration treatments.

Stability has been shown to be influenced by the size and homogeneity of the emulsion. The preferred emulsion consists of a suspension of sub-micron particles, with a mean size of no greater than 200 nanometers. A stable dispersion in this size range is not easily achieved, but has the benefit that it is expected to circulate longer in the bloodstream. Further, less of the stable dispersion is phagocytized non-specifically by the reticuloendothelial system. As a result the drug is more likely to reach its therapeutic target. Thus, a preferred drug emulsion will be designed to be actively taken up by the target cell or organ, and is targeted away from the RES.

The use of vitamin E in emulsions is known. In addition to the hundreds of examples where vitamin E in small quantities [for example, less than 1%, RT Lyons. Pharm Res 13(9): S-226, (1996) "Formulation development of an injectable oil-in-water emulsion containing the lipophilic antioxidants K-tocopherol and P-carotene"] is used as an anti-oxidant in emulsions, the first primitive, injectable vitamin E emulsions per se were made by Hidiroglou for dietary supplementation in sheep and for research on the pharmacokinetics of vitamin E and its derivatives. Hidiroglou M and Karpinski K. (1988) Brit J Nutrit 59:509–518.

For mice, an injectable form of vitamin E was prepared by Kato and coworkers. Kato Y., et al. (1993) Chem Pharm Bull 41(3):599–604. Micellar solutions were formulated with Tween 80, Brij 58 and HCO-60. Isopropanol was used as a co-solvent, and was then removed by vacuum evaporation; the residual oil glass was then taken up in water with vortexing as a micellar suspension. An emulsion was also prepared by dissolving vitamin E with soy phosphatidycholine (lecithin) and soybean oil. Water was added and the emulsion prepared with sonication.

In 1983, E-Ferol, a vitamin E emulsion was introduced for vitamin E supplementation and therapy in neonates. Alade SL et al. (1986) Pediatrics 77(4):593–597. Within a few months over 30 babies had died as a result of receiving the product, and the product was promptly withdrawn by FDA order. The surfactant mixture used in E-Ferol to emulsify 25 mg/mL vitamin E consisted of 9% Tween 80 and 1% Tween 20. These surfactants seem ultimately to have been responsible for the unfortunate deaths. This experience illustrates the need for improved formulations and the importance of selecting suitable biocompatible surfactants and carefully monitoring their levels in parenteral emulsions and.

An alternative means of solubilizing low solubility compounds is direct solubilization in a non-aqueous milieu, for example alcohol (such as ethanol) dimethylsulfoxide or triacetin. An example in PCT application WO 95/11039 describes the use of vitamin E and the vitamin E derivative TPGS in combination with ethanol and the immunosuppressant molecule cyclosporin. Alcohol-containing solutions can be administered with care, but are typically given by intravenous drip to avoid the pain, vascular irritation and toxicity associated with bolus injection of these solutions.

Problems with pharmaceutical formulations in non-aqueous solvents and solubilizers such as alcohol (ethanol, isopropanol, benzyl alcohol, etc.) relate to the ability of these solvents to extract toxic substances, for example plasticizers, from their containers. The current commercial formulation for the anti-cancer drug paclitaxel, for example, consists of a mixture of hydroxylated castor oil and ethanol, and rapidly extracts plasticizers such as di-(2-ethylhexyl)-phthalate from commonly used intravenous infusion tubing and bags. Adverse reactions to the plasticizers have been reported, such as respiratory distress, necessitating the use of special infusion systems at extra expense and time. Waugh, et al. (1991) Am J Hosp Pharmacists 48:1520.

In light of these problems, it can be seen that the ideal emulsion vehicle would be inexpensive, non-irritating or even nutritive and palliative in itself, terminally sterilizable by either heat or filtration, stable for at least, year under controlled storage conditions, accommodate a wide variety of water insoluble and poorly soluble drugs and be substantially ethanol-free. In addition to those drugs which are lipophilic and dissolve in oils, also needed is a vehicle which will stabilize, and carry in the form of an emulsion, drugs which are poorly soluble in lipids and in water.

SUMMARY OF THE INVENTION

In order to meet these needs, the present invention is directed to pharmaceutical compositions including: α-tocopherol, a surfactant or mixtures of surfactants, with and without an aqueous phase, and a therapeutic agent wherein the composition is in the form of an emulsion, micellar solution or a self-emulsifying drug delivery system. In a preferred form, the solution is substantially ethanol-free.

The pharmaceutical compositions can be stabilized by the addition of various amphiphilic molecules, including anionic, nonionic, cationic, and zwitterionic surfactants. Preferably, these molecules are PEGylated surfactants and optimally PEGylated α-tocopherol.

The amphiphilic molecules further include surfactants such as ascorbyl-6 palmitate; stearylamine; sucrose fatty acid esters, various vitamin E derivatives and fluorine-containing surfactants, such as the Zonyl brand series and a polyoxypropylene-polyoxyethylene glycol nonionic block copolymer.

The therapeutic agent of the emulsion may be a chemotherapeutic agent preferably a taxoid analog and most preferably, paclitaxel.

The emulsions of the invention can comprise an aqueous medium when in the form of an emulsion or micellar solution. This medium can contain various additives to assist in stabilizing the emulsion or in rendering the formulation biocompatible.

The pharmaceutical compositions of the invention are typically formed by dissolving a therapeutic agent in ethanol to form a therapeutic agent solution. α-tocopherol is then added to the therapeutic agent solution to form an α-tocopherol and therapeutic agent solution. Next, the ethanol is removed to form a substantially ethanol-free α-tocopherol and therapeutic agent solution. The substantially ethanol free α-tocopherol and therapeutic agent solution is blended with and without an aqueous phase incorporating a surfactant to form a pre-emulsion. For IV delivery the pre-emulsion is then homogenized to form a fine emulsion. For oral delivery, the pre-emulsion is typically encapsulated in a gelatin capsule.

BRIEF DESCRIPTION OF THE DRAWINGS

The invention will be better understood by reference to the figures, in which.

DETAILED DESCRIPTION OF THE INVENTION

Figure 1A:
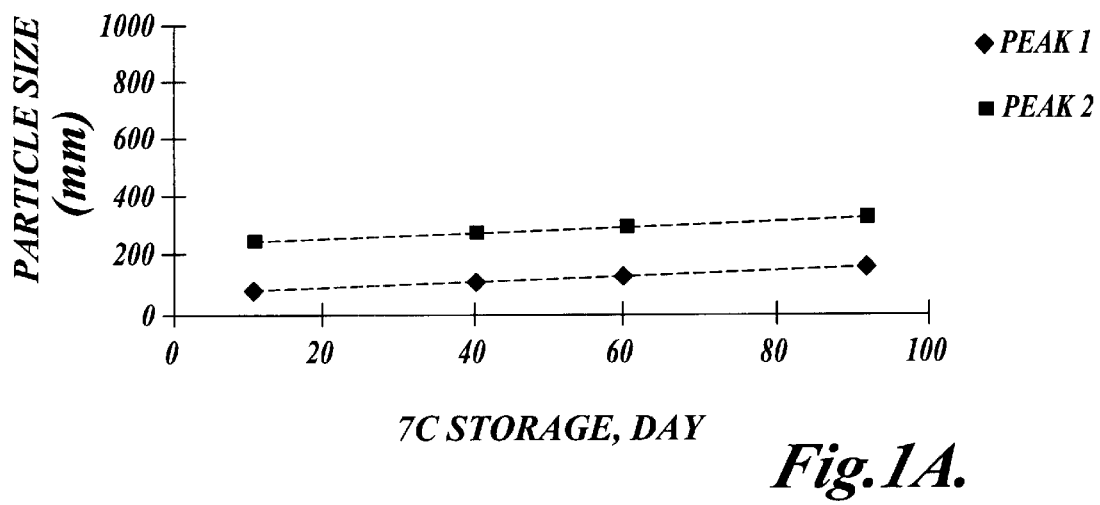
FIG. 1A shows the particle size of a paclitaxel emulsion (QWA) at 7° C. over time.

To ensure a complete understanding of the invention the following definitions are provided:

α-tocopherol: α-tocopherol, also known as vitamin E, is an organic molecule with the following chemical structure (Scheme I):

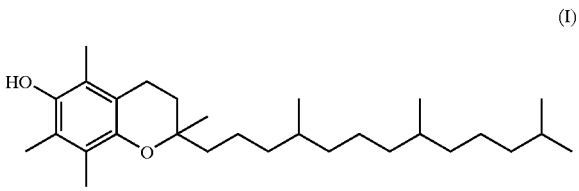

(I)

In addition to its use as a primary solvent, α-tocopherol and its derivatives are useful as a therapeutic agents.

Surfactants: Surface active group of amphiphilic molecules which are manufactured by chemical processes or purified from natural sources or processes. These can be anionic, cationic, nonionic, and zwitterionic. Typical surfactants are described in Emulsions: Theory and Practice, Paul Becher, Robert E. Krieger Publishing, Malabar, Fla., 1965; Pharmaceutical Dosage Forms: Dispersed Systems Vol. I, Martin M. Rigear, Surfactants and U.S. Pat. No. 5,595,723 which is assigned to the assignee of this invention, Sonus Pharmaceuticals. All of these references are hereby incorporated by reference.

TPGS: TPGS or PEGylated vitamin E is a vitamin E derivative in which polyethylene glycol subunits are attached by a succinic acid diester at the ring hydroxyl of the vitamin E molecule. TPGS stands for D-α-tocopherol polyethyleneglycol 1000 succinate (MW=530). TPGS is a non-ionic surfactant (HLB=16–18) with the structure of Scheme II Hydrophile-lipophile balance: An empirical formula used to index surfactants. Its value varies from 1–45 and in the case of non-ionic surfactants from about 1–20. In general for lipophilic surfactants the HLB is less than 10 and for hydrophilic ones the HLB is greater than 10.

Biocompatible: Capable of performing functions within or upon a living organism in an acceptable manner, without undue toxicity or physiological or pharmacological effects.

Substantially ethanol-free: A composition having an ethanol concentration less than about 1.0% (w/v) ethanol.

Emulsion: A colloidal dispersion of two immiscible liquids in the form of droplets, whose diameter, in general, are between 0.1 and 3.0 microns and which is typically optically opaque, unless the dispersed and continuous phases are refractive index matched. Such systems possess a finite stability, generally defined by the application or relevant

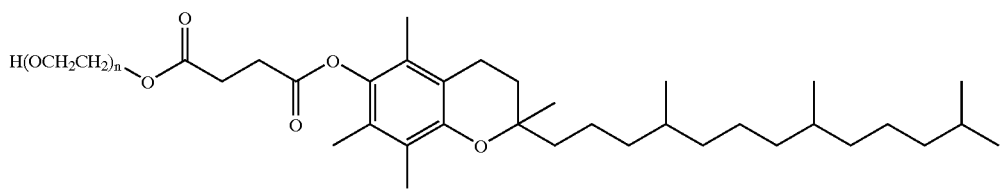

(II)

Various chemical derivatives of vitamin E TPGS including ester and ether linkages of various chemical moieties are included within the definition of vitamin E TPGS.

Polyethylene glycol : Polyethylene glycol (PEG) is a hydrophilic, polymerized form of ethylene glycol, consisting of repeating units of the chemical structure—(CH$_2$—CH$_2$—O—).

AUC: AUC is the area under the plasma concentration-time, commonly used in pharmacokinetics to quantitate the percentage of drug absorption and elimination. A high AUC generally indicates that the drug will successfully reach the target tissue or organ.

Poloxamers or Pluronics: are synthetic block copolymers of ethylene oxide and propylene oxide having the general structure:

The following variants based on the values of a and b are commercially available from BASF Performance Chemicals (Parsippany, N.J. under the trade name Pluronic and which consist of the group of surfactants designated by the CTFA name of Poloxamer 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used poloxamers 124, 188, 237, 338 and 407 the values of a and b are 12/20, 79/28, 64/37, 141/44 and 101/56, respectively.

Solutol HS-15: is a polyethylene glycol 660 hydroxystearate manufactured by BASF (Parsippany, N.J.). Apart from free polyethylene glycol and its monoesters, di-esters are also detectable. According to the manufacturer, a typical lot of Solutol HS-15 contains approximately 30% free polyethylene glycol and 70% polyethylene glycol esters.

Other surfactants: Other surfactants useful in the invention include ascorbyl1–6 palmitate (Roche Vitamins, Nutley N.J.), stearylamine, and sucrose fatty acid esters (Mitsubishi Chemicals). Custom surfactants include those compounds with polar water-loving heads and hydrophobic tails, such as a vitamin E derivative comprising a peptide bonded polyglutamate attached to the ring hydroxyl and pegylated phytosterol.

reference system, which may be enhanced by the addition of amphiphilic molecules or viscosity enhancers.

Microemulsion: A thermodynamically stable isotropically clear dispersion of two immiscible liquids, such as oil and water, stabilized by an interfacial film of surfactant molecules. The microemulsion has a mean droplet diameter of less than 200 nm, in general between 10–50 nm. In the absence of water, mixtures of oil(s) and non-ionic surfactant (s) form clear and isotropic solutions that are known as self-emulsifying drug delivery systems (SEDDS) and have successfully been used to improve lipophilic drug dissolution and oral absorption Aqueous Medium: A water-containing liquid which can contain pharmaceutically acceptable additives such as acidifying, alkalizing, buffering, chelating, complexing and solubilizing agents, antioxidants and antimicrobial preservatives, humectants, suspending and/or viscosity modifying agents, tonicity and wetting or other biocompatible materials.

Therapeutic Agent: Any compound natural of synthetic which has a biological activity, is soluble in the oil phase and has an octanol-buffer partition coefficient (Log P) of at least 2 to ensure that the therapeutic agent is preferentially dissolved in the oil phase rather than the aqueous phase.

This includes peptides, non-peptides and nucleotides. Lipid conjugates/prodrugs of water soluble molecules are within the scope of therapeutic agent.

Chemotherapeutic: Any natural or synthetic molecule which is effective against one or more forms of cancer, and particularly those molecules which are slightly or completely lipophilic or which can be modified to be lipophilic. This definition includes molecules which by their mechanism of action are cytotoxic (anti-cancer agents), those which stimulate the immune system (immune stimulators) and modulators of angiogenesis. The outcome in either case is the slowing of the growth of cancer cells.

Chemotherapeutics include Taxol (paclitaxel) and related molecules collectively termed taxoids, taxines or taxanes. The structure of paclitaxel is shown in the figure below (Scheme III).

(III)

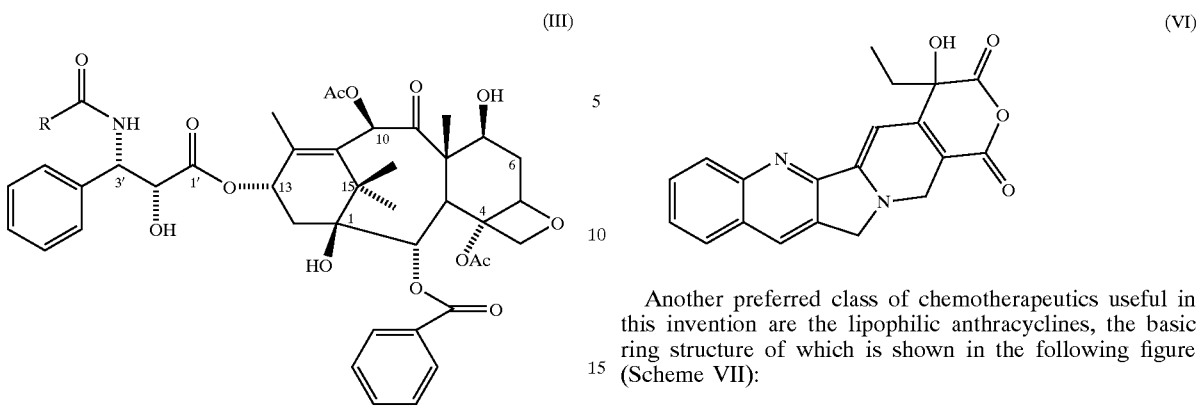

Included within the definition of "taxoids" are various modifications and attachments to the basic ring structure (taxoid nucleus) as may be shown to be efficacious for reducing cancer cell growth and to partition into the oil (lipid phase) and which can be constructed by organic chemical techniques known to those skilled in the art. The structure of the taxoid nucleus is shown in Scheme IV.

(IV)

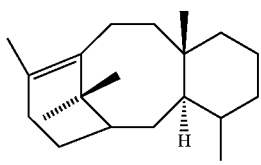

Chemotherapeutics include podophyllotoxins and their derivatives and analogues. The core ring structure of these molecules is shown in the following figure (Scheme V):

(V)

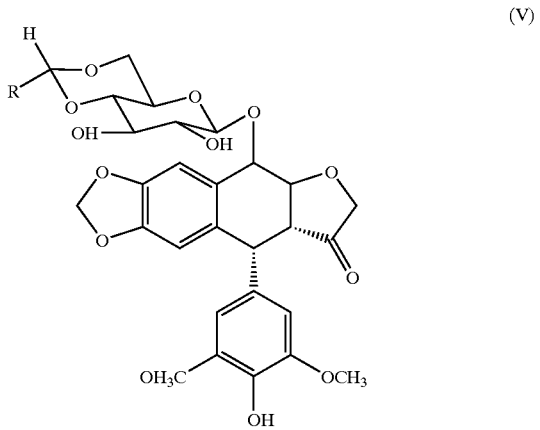

Another important class of chemotherapeutics useful in this invention are camptothecins, the basic ring structure of which is shown in the following figure, but includes any derivatives and modifications to this basic structure which retain efficacy and preserve the lipophilic character of the moleculeshown below (Scheme VI).

(VI)

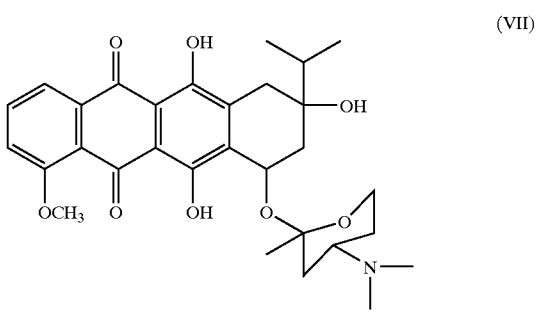

Another preferred class of chemotherapeutics useful in this invention are the lipophilic anthracyclines, the basic ring structure of which is shown in the following figure (Scheme VII):

(VII)

Suitable lipophilic modifications of Scheme VII include substitutions at the ring hydroxyl group or sugar amino group.

Another important class of chemotherapeutics are compounds which are lipophilic or can be made lipophilic by molecular chemosynthetic modifications well known to those skilled in the art, for example by combinatorial chemistry and by molecular modelling, and are drawn from the following list: Taxotere, Amonafide, Illudin S, 6-hydroxymethylacylfulvene Bryostatin 1, 26-succinylbryostatin 1, Palmitoyl Rhizoxin, DUP 941, Mitomycin B, Mitomycin C, Penclomedine. Interferon α2b, angiogenesis inhibitor compounds, Cisplatin hydrophobic complexes such as 2-hydrazino-4,5-dihydro-1H-imidazole with platinum chloride and 5-hydrazino-3,4-dihydro-2H-pyrrole with platinum chloride, vitamin A, vitamin E and its derivatives, particularly tocopherol succinate.

Other compounds useful in the invention include: 1,3-bis (2-chloroethyl)-1-nitrosurea ("carmustine" or "BCNU"), 5-fluorouracil, doxorubicin ("adriamycin"), epirubicin, aclarubicin, Bisantrene (bis(2-imidazolen-2-ylhydrazone)-9, 10-anthracenedicarboxaldehyde, mitoxantrone, methotrexate, edatrexate, muramyl tripeptide, muramyl dipeptide, lipopolysaccharides, 9-b-d-arabinofairanosyladenine ("vidarabine") and its 2-fluoro derivative, resveratrol, retinoic acid and retinol, Carotenoids, and tamoxifen.

Other compounds useful in the application of this invention include: Palmitoyl Rhizoxin, DUP 941, Mitomycin B, Mitomycin C, Penclomedine, Interferon α2b, Decarbazine, Lonidamine, Piroxantrone, Anthrapyrazoles, Etoposide, Camptothecin, 9-aminocamptothecin, 9-nitrocamptothecin, camptothecin-11 ("Irinotecan"), Topotecan, Bleomycin, the Vinca alkaloids and their analogs [Vincristine, Vinorelbine, Vindesine, Vintripol, Vinxaltine, Ancitabine], 6-aminochrysene, and navelbine.

Other compounds useful in the application of the invention are mimetics of taxol, eleutherobins, sarcodictyins, discodermolides and epothiolones.

Taking into account these definitions, the present invention is directed to pharmaceutical compositions in the form of emulsions, micellar solutions or self-emulsifying drug delivery systems which are substantially free of ethanol solvent.

The therapeutic agents of the compositions of this invention can initially be solublized in ethanol. However, the ethanol is removed in order to form a substantially ethanol-free composition. The ethanol concentration is less than 1% (w/v), preferably less than 0.5%, and most preferably less than 0.3%. The therapeutic agents can also be solubilized in methanol, propanol, chloroform, isopropanol, butanol and pentanol. These solvents are also removed prior to use.

The compositions of the invention contain α-tocopherol as a carrier for therapeutic drugs, which can be administered to animals or humans via intravascular, oral, intramuscular, cutaneous and subcutaneous routes. Specifically, the emulsions can be given by any of the following routes, among others: intraabdominal, intraarterial, intraarticular, intracapsular, intracervical, intracranial, intraductal, intradural, intralesional, intralocular, intralumbar, intramural, intraocular, intraoperative, intraparietal, intraperitoneal, intrapleural, intrapulmonary, intraspinal, intrathoracic, intratracheal, intratympanic, intrauterine, and intraventricular. The emulsions of the present invention can be nebulized using suitable aerosol propellants which are known in the art for pulmonary delivery of lipophilic compounds.

In its first aspect, the invention is directed to the use of α-tocopherol as the hydrophobic dispersed phase of emulsions containing water insoluble, poorly water soluble therapeutic agents, water soluble therapeutic agents which have been modified to be less water soluble or mixtures thereof. Also called vitamin E, α-tocopherol is not a typical lipid oil. It has a higher polarity than most lipid oils, particularly triglycerides, and is not saponifiable. It has practically no solubility in water.

In the second aspect, the invention is a an α-tocopherol emulsion in the form of a self-emulsifying system where the system is to be used for the oral administration of water insoluble (or poorly water soluble or water soluble agents modified to be less water soluble or mixtures thereof) drugs where that is desired. In this embodiment, an oil phase with surfactant and drug or drug mixture is encapsulated into a soft or hard gelatin capsule. Suitable solidification agents with melting points in the range of 40 to 60° C. such as high molecular weight polyethylene glycols (MW>1000) and glycerides such as those available under the trade name Gellucires (Gattefose Corp. Saint Priest, France) can be added to allow filling of the formulation into a hard gelatin capsule at high temperature. Semi-solid formulations are formed upon room temperature equilbration. Upon dissolution of the gelatin in the stomach and duodenun, the oil is released and forms a fine emulsion with a mean droplet diameter of between 2–5 microns spontaneously. The emulsion is then taken up by the microvilli of the intestine and released into the bloodstream.

In a third aspect, the invention comprises microemulsions containing α-tocopherol. Microemulsions refer to a subclass of emulsions where the emulsion suspension is essentially clear and indefinitely stable by virtue of the extremely small size of the oil/drug microaggregates dispersed therein.

In a fourth aspect of the invention, PEGylated vitamin E (TPGS) is used as a primary surfactant in emulsions of vitamin E. PEGylated vitamin E is utilized as a primary surfactant, a stabilizer and also as a supplementary solvent in emulsions of vitamin E. Polyethylene glycol (PEG) is also useful as a secondary solvent in the emulsions of this invention.

The α-tocopherol concentration of the emulsions of this invention can be from about 2 to about 10% w/v. The ratio of α-tocopherol to TPGS is optimally from about 1:1 to about 10:1 (w/w).

The emulsions of the invention may further include surfactants such as ascorbyl-6 palmitate; stearylamine; sucrose fatty acid esters and various vitamin E derivatives comprising α-tocopherol nicotinate, tocopherol phosphate, and nonionic, synthetic surfactant mixtures, containing a fluorine-containing surfactant, such as the Zonyl brand series and a polyoxypropylene-polyoxyethylene glycol nonionic block copolymer.

The emulsions of the invention can comprise an aqueous medium. The aqueous phase has an osmolality of approximately 300 mOsm and may include potassium or sodium chloride sorbitol, mannitol, polyethylene glycol, propylene glycol albumin, polypep and mixtures thereof. This medium can also contain various additives to assist in stabilizing the emulsion or in rendering the formulation biocompatible. Acceptable additives include acidifying agents, alkalizing agents, antimicrobial preservatives, antioxidants, buffering agents, chelating agents, suspending and/or viscosity-increasing agents, and tonicity agents. Preferably, agents to control the pH, tonicity, and increase viscosity are included. Optimally, a tonicity of at least 250 mOsm is achieved with an agent which also increases viscosity, such as sorbitol or sucrose.

The emulsions of the invention for intravenous injection have a article size of 10 to 500 nm, preferably 10 to 200 nm and most preferably 10 to 100 nm. For intravenous emulsions, the spleen and liver will eliminate particles greater than 500 mn in size through the RES.

A preferred form of the invention includes paclitaxel, a very water-insoluble cytotoxin used in the treatment of uterine cancer and other carcinomas. An emulsion composition of the present invention comprises a solution of vitamin E containing paclitaxel at a concentration of up to 20 mg/mL, four times that currently available by prescription, and a biocompatible surfactant such that the emulsion microdroplets are less than 0.2 microns and are terminally sterilizable by filtration.

A further embodiment of the invention is a method of treating carcinomas comprising the parenteral administration of a bolus dose of paclitaxel in vitamin E emulsion with and without PEGylated vitamin E by intravenous injection once daily or every second day over a therapeutic course of several weeks. Such method can be used for the treatment of carcinomas of the breast, lung, skin and uterus.

The general principles of the present invention may be more fully appreciated by reference to the following non-limiting examples.

EXAMPLES

Example 1

Dissolution of Paclitaxel in α-tocopherol

α-Tocopherol was obtained from Sigma Chemical Company (St Louis Mo.) in the form of a synthetic dl-α-tocopherol of 95% purity prepared from phytol. The oil was amber in color and very viscous. Paclitaxel was purchased from Hauser Chemical Research (Boulder Colo.), and was 99.9% purity by HPLC. Paclitaxel 200 mg was dissolved in 6 mL of dry absolute ethanol (Spectrum Chemical Manufacturing Corp, Gardenia Calif.) and added to 1 gm α-tocopherol. The ethanol was then removed by vacuum at 42° C. until the residue was brought to constant weight. Independent studies showed that the ethanol content was less than 0.3% (w/v).

The resultant solution was clear, amber and very viscous, with a nominal concentration of 200 mg/gm (w/w) paclitaxel in α-tocopherol. Higher concentrations of Paclitaxel (up to 400 mg/gm, w/w) can be solubilized in α-tocopherol.

Example 2
Anionic Surfactant Used to Prepare α-tocopherol Emulsions

Paclitaxel 2 gm in 10 gm of α-tocopherol, prepared as described in Example 1, was emulsified with ascorbyl palmitate as the triethanolamine salt by the following method. A solution consisting of ascorbic acid 20 mM was buffered to pH 6.8 with triethanolamine as the free base to from 2× buffer. 50 mL of the 2× buffer was placed in a Waring blender. 0.5 gm of ascorbyl-6-palmitate (Roche Vitamins and Fine Chemicals, Nutley N.J.), an anionic surfactant, was added and the solution blended at high speed for 2 min at 40° C. under argon. The α-tocopherol containing paclitaxel was then added into the blender with the surfactant and buffer. Mixing was continued under argon until a coarse, milky, pre-emulsion was obtained, approximately after 1 min at 40° C. Water for injection was then added, bringing the final volume to 100 mL.

The pre-emulsion was transferred to the feed vessel of a Microfluidizer Model 110Y (Microfluidics Inc, Newton Mass.). The unit was immersed in a bath to maintain a process temperature of approximately 60° C. during homogenization, and was flushed with argon before use. After priming, the emulsion was passed through the homogenizer in continuous recycle for 10 minutes at a pressure gradient of about 18 kpsi across the interaction head. The flow rate was about 300 mL/min, indicating that about 25 passes through the homogenizer resulted.

The resultant paclitaxel emulsion in an α-tocopherol vehicle was bottled in amber vials under argon and stored with refrigeration at 7° C. and 25° C. Samples were taken at discrete time intervals for particle sizing and chemical analysis.

Data taken with a Nicomp Model 370 Submicron Particle Sizer (Particle Sizing Systems Inc, Santa Barbara Calif.) showed that the emulsion had a mean particle diameter of 280 nm.

Example 3
Use of PEGylated Vitamin E (TPGS)

A ternary phase diagram was constructed for α-tocopherol, PEGylated vitamin E (TPGS, vitamin-E polyoxyethyleneglycol-1000-succinate, obtained from Eastman Chemical Co., Kingsport Tenn.), and water. TPGS was first melted at 42° C. and mixed gravimetrically with α-tocopherol at various proportions from 1 to 100% TPGS, the balance being α-tocopherol. Mixtures were miscible at all concentrations. Water was then added to each mixture in such a way that the final water concentration was increased stepwise from zero to 97.5%. At each step, observations were made of the hase behavior of the mixture. As appropriate, mixing was performed by vortexing and sonication, and the mixture was heated or centrifuged to assess its phase composition.

A broad area of biphasic o/w emulsions suitable for parenteral administration was found at water concentrations above 80%. The emulsions formed were milky white, free flowing liquids that contained disperse α-tocopherol microparticles stabilized by non-ionic surfactant. Also in this area, microemulsions potentially suitable as drug carriers were observed at TPGS to oil ratios above about 1:1. At lower water content, a broad area containing transparent gels (reverse emulsions) was noted. Separating the two areas (high and low water content) is an area composed of opaque, soap-like liquid crystals.

Phase diagrams of α-tocopherol with surfactant combinations, for example TPGS with a nonionic, anionic or cationic co-surfactant (for example glutamyl stearate, ascorbyl palmitate or Pluronic F-68), or drug can be prepared in a similar manner.

Example 4
α-Tocopherol Emulsion for Intravenous Delivery of Paclitaxel

A formulation of the following composition was prepared:

| | |
|---|---|
| Paclitaxel | 1.0 gm % |
| α-tocopherol | 3.0 gm % |
| TPGS | 2.0 gm % |
| Ascorbyl-6-Palmitate | 0.25 gm % |
| Sorbitol | 5.0 gm % |
| Triethanolamine | to pH 6.8 |
| Water | qs to 100 mL |

The method of preparation was as follows: synthetic α-tocopherol (Roche Vitamins, Nutley N.J.), paclitaxel (Hauser, Boulder Colo.), ascorbyl 6-palmitate (Aldrich Chemical Co, Milwaukee Wis.) and TPGS were dissolved in 10 volumes of anhydrous undenatured, ethanol (Spectrum Quality Products, Gardenia Calif.) with heating to 40–45° C. The ethanol was then drawn off with vacuum until no more than 0.3% remained by weight.

Pre-warmed aqueous solution containing a biocompatible osmolyte and buffer were added with gentle mixing and a white milk formed immediately. This mixture was further improved by gentle rotation for 10 minutes with continuous warming at 40–45° C. This pre-mixture at about pH 7 was then further emulsified as described below.

The pre-mixture at 40–45° C. was homogenized in an Avestin C5 homogenizer (Avestin, Ottawa Canada) at 26 Kpsi for 12 minutes at 44° C. The resultant mixture contained microparticles of α-tocopherol with a mean size of about 200 nm. Further pH adjustment was made with an alkaline 1 M solution of triethanolamine (Spectrum Quality Products).

In order to avoid gelation of the TPGS during the early stage of emulsification, all operations were performed above 40° C. and care was taken to avoid exposure of the solutions to cold air by covering all vessels containing the mixture. Secondly, less than 2% TPGS should generally be dissolved in α-tocopherol oil before pre-emulsification, the balance of the TPGS being first dissolved in the aqueous buffer before the pre-emulsion is prepared. The solution gels at concentrations of TPGS higher than 2%.

Figure 1B:
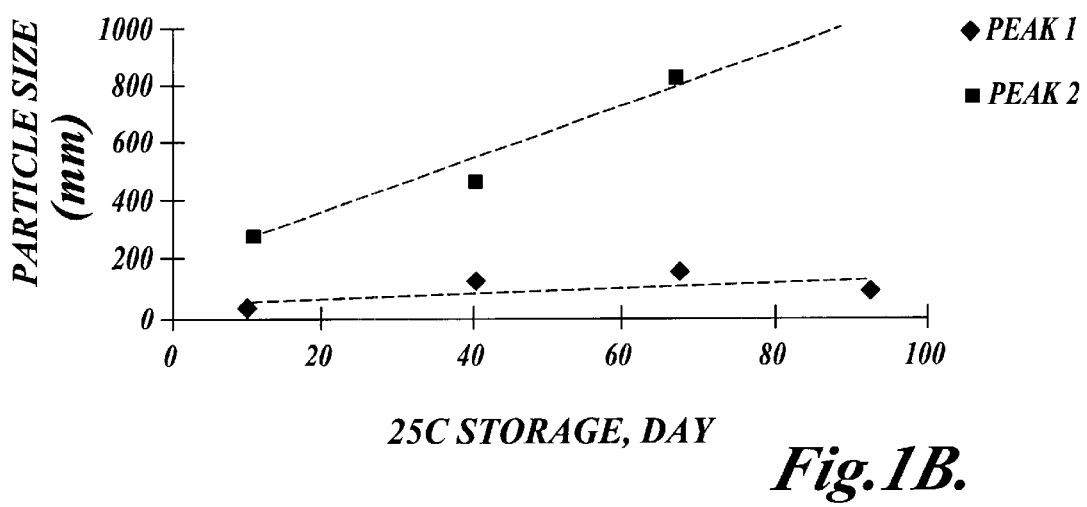
FIG. 1B shows the particle size of a paclitaxel emulsion (QWA) at 25° C. over time.

Physical stability of the emulsion was then examined by placing multiple vials on storage at 4° C. and 25° C. Over several months, vials were periodically withdrawn for particle sizing. Mean particle size, as determined with the Nicomp Model 370 (Particle Sizing Systems, Santa Barbara Calif.), is shown for the two storage temperatures in FIG. 1. The particle size distribution was bi-modal.

Example 5
Chemical Stability of Paclitaxel in an α-tocopherol Emulsion

Figure 2:
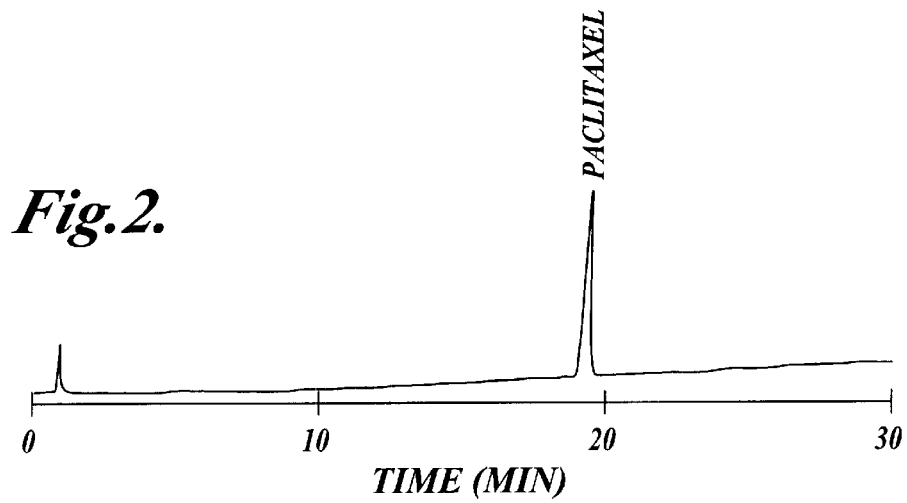
FIG. 2 is an HPLC chromatogram showing the integrity of a paclitaxel in an emulsion as described in Example 5.

After emulsification, the formulation of Example 4 was analyzed for paclitaxel on a Phenosphere CN column (5 microns, 150×4.6 mm). The mobile phase consisted of a methanol/water gradient, with a flow rate of 1.0 mL/min. A UV detector set at 230 nm was used to detect and quantitate paclitaxel. A single peak was detected (FIG. 2), which had a retention time and mass spectrogram consistent with native reference paclitaxel obtained from Hauser Chemical (Boulder Colo.).

Figure 3A:
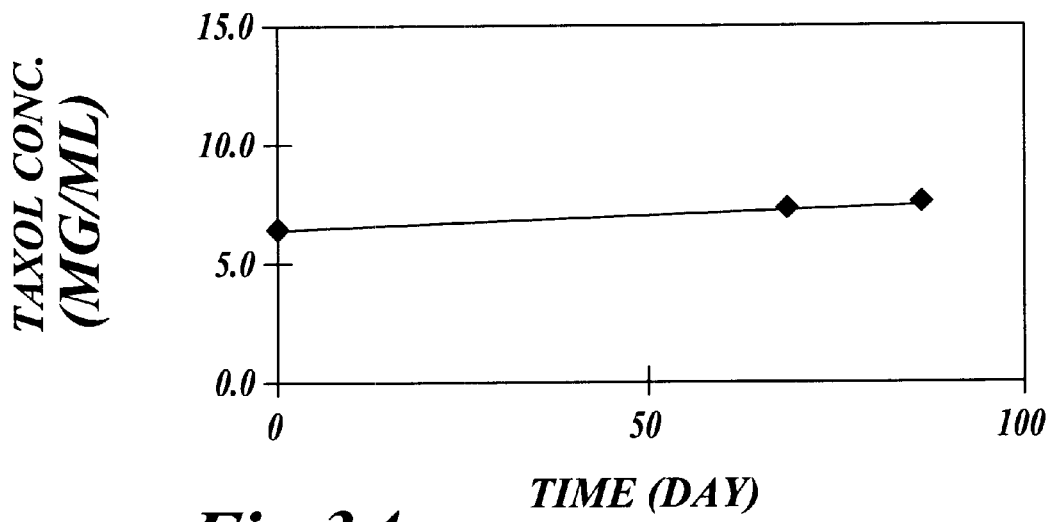
FIG. 3A shows the paclitaxel concentration of a paclitaxel emulsion (QWA) at 4° C. over time.
Figure 3B:
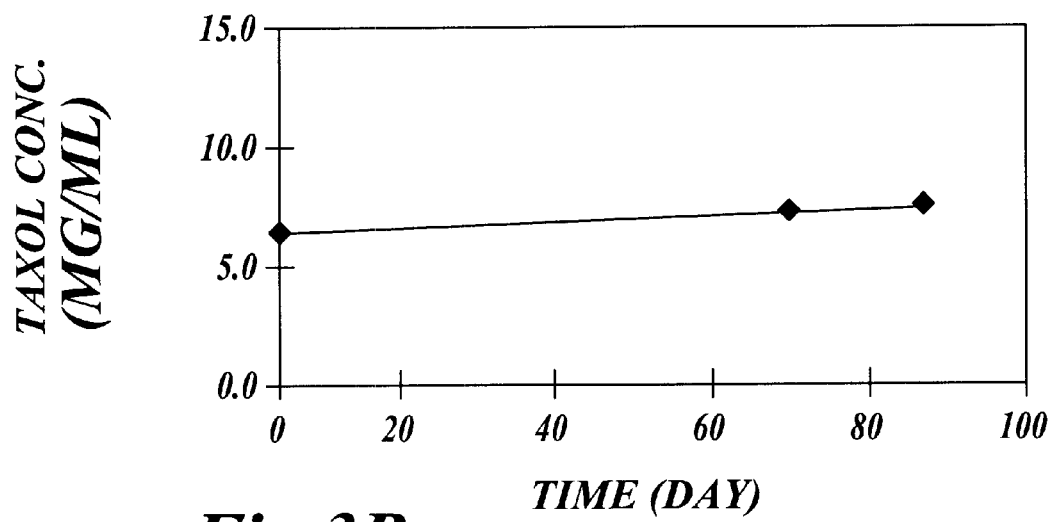
FIG. 3B shows the paclitaxel concentration of a paclitaxel emulsion (QWA) at 25° C. over time.

Chemical stability of the emulsion of example 4 was examined by HPLC during storage. The data of FIG. 3 demonstrate that paclitaxel remains stable in the emulsion for periods of at least 3 months, independent of the storage temperature. Taken together, the data of FIG. 2 and 3 demonstrate successful retention of drug potency and emulsion stability when stored at 4° C. for a period of at least 3 months.

Example 6
Paclitaxel Emulsion Formulation QWA

An emulsion of paclitaxel 10 mg/ml for intravenous drug delivery, having the following composition, was prepared as described in Example 4.

| | |
|---|---|
| Paclitaxel | 1.0 gm % |
| α-tocopherol | 3.0 gm % |
| TPGS | 1.5 gm % |
| Ascorbyl-6-Palmitate | 0.25 gm % |
| Sorbitol | 4.0 gm % |
| Triethanolamine | to pH 6.8 |
| Water | qs to 100 mL |

Example 7
Paclitaxel Emulsion Formulation QWB

A second emulsion of paclitaxel 10 mg/ml for intravenous drug delivery, having the following composition, was prepared as described in Example 4.

| | |
|---|---|
| Paclitaxel | 1.0 gm % |
| α-tocopherol | 3.0 gm % |
| TPOS | 1.5 gm % |
| Solutol HS-15 | 1.0 gm % |
| Sorbitol | 4.0 gm % |
| Triethanolamine | to pH 6.8 |
| Water | qs to 100 mL |

Solutol HS-15 is a product of BASF Corp, Mount Olive N.J.

Example 8
10 mg/mL Paclitaxel Emulsion Formulation QWC

A third emulsion formulation of paclitaxel 10 mg/ml was prepared as follows using Poloxamer 407 (BASF Corp, Parsippany N.J.) as a co-surfactant.

| | |
|---|---|
| Paclitaxel | 1.0 gm % |
| α-tocopherol | 6.0 gm % |
| TPGS | 3.0 gm % |
| Poloxamer 407 | 1.0 gm % |
| Sorbitol | 4.0 gm % |
| Triethanolamine | to pH 6.8 |
| Water for injection | qs to 100 mL |

In this example, 1.0 gm Poloxamer 407 and 1.0 gm paclitaxel were dissolved in 6.0 gm α-tocopherol with ethanol 10 volumes and gentle heating. The ethanol was then removed under vacuum. Separately, an aqueous buffer was prepared by dissolving 3.0 gm TPGS and 4.0 gm sorbitol in a final volume of 90 mL water for injection. Both oil and water solutions were warmed to 45° C. and mixed with sonication to make a pre-emulsion. A vacuum was used to remove excess air from the pre-emulsion before homogenization.

Homogenization was performed in an Avestin C5 as already described. The pressure differential across the homogenization valve was 25 kpsi and the temperature of the feed was 42–45C. A chiller was used to ensure that the product exiting the homogenizer did not exceed a temperature of 50° C. Flow rates of 50 mL/min were obtained during homogenization. After about 20 passes in a recycling mode, the emulsion became more translucent. Homogenization was continued for 20 min. Samples were collected and sealed in vials as described before. A fine α-tocopherol emulsion for intravenous delivery of paclitaxel was obtained. The mean particle diameter of the emulsion was 77 nm. Following 0.22 µ sterile filtration through a 0.22 micron Durapore filter (Millipore Corp, Bedford Mass.), the emulsion was filled in vials and stored at 4° C. until used for intravenous injection.

Example 9
5 mg/mL Paclitaxel Emulsion Formulation QWC

An additional emulsion of paclitaxel was prepared as described in Example 8 but incorporating 5 instead of 10 mg/ml of the drug. The composition of this emulsion is as follows:

| | |
|---|---|
| Paclitaxel | 0.5 gm % |
| α-tocopherol | 6.0 gm % |
| TPGS | 3.0 gm % |
| Poloxamer 407 | 1.0 gm % |
| Sorbitol | 4.0 gm % |
| Triethanolamine | to pH 6.8 |
| Water for injection | qs to 100 mL |

Following homogenization as described in example 8, a somewhat translucent emulsion of α-tocopherol and paclitaxel with a mean particle diameter of 52 nm was obtained. Following sterile filtration through a 0.22 micron Durapore filter (Millipore Corp, Bedford Mass.), the emulsion was filled in vials and stored at 4° C. until used for intravenous injection. Drug losses on filtration were less than 1%.

Example 10
Paclitaxel Emulsion Formulation QWD

A fifth emulsion of α-tocopherol for intravenous administration of paclitaxel was prepared as follows:

| | |
|---|---|
| Paclitaxel | 0.5 gm % |
| α-tocopherol | 6.0 gm % |
| TPGS | 3.0 gm % |
| Poloxamer 407 | 1.5 gm % |
| Polyethyleneglycol 200 | 0.7 gm % |
| Sorbitol | 4.0 gm % |
| Triethanolamine | to pH 6.8 |
| Water for injection | qs to 100 mL |

Synthetic (α-tocopherol USP-FCC obtained from Roche Vitamins (Nutley, N.J.) was used in this formation. Polyethyleneglycol 200 (PEG-200) was obtained from Sigma Chemical Co.

Following homogenization, a somewhat translucent emulsion with a mean particle diameter of 60 nm was obtained. Following 0.22µ sterile filtration through a 0.22 micron Durapore filter (Millipore Corp, Bedford Mass.), the emulsion was filled in vials and stored at 4° C. until used for intravenous injection. Drug losses on filtration were less than 1%.

Example 11
Dissolution of Paclitaxel in TPGS and Preparation of Micellar Solutions We observed good solubility of paclitaxel in TPGS, about 100 mg drug per 1.0 gm of TPGS. Micellar solutions of TPGS containing paclitaxel were prepared as follows. A stock solution of paclitaxel in TPGS was made up by dissolving 90 mg paclitaxel in 1.0 gm TPGS at 45 ° C. with ethanol, which was then removed under vacuum. Serial dilutions were then prepared by diluting the paclitaxel stock with additional TPGS to obtain paclitaxel in TPGS at concentrations of 0.1, 1, 5, 10, 25, 50, 75 and 90 mg/mL. Using fresh test tubes, 100 mg of each paclitaxel concentration in TPGS was dissolved in 0.9 mL water. All test tubes were mixed by vortex and by sonication at 45° C. Clear micellar solutions in water were obtained corresponding to final paclitaxel concentrations of 0.01, 0.1, 0.5, 1.0, 2.5, 5.0, 7.5 and 9.0 mg/mL.

A Nicomp Model 370 laser particle sizer (Particle Sizing Systems, 10 Santa Barbara Calif.) was used to examine the solutions. Particle sizes on the order of 10 nm were obtained, consistent with the presence of micelles of TPGS and paclitaxel.

Micellar solutions of paclitaxel in TPGS containing up to 2.5 mg/mL paclitaxel were stable for at least 24 hr whereas those at 5.0, 7.5 and 9.0 mg/mL were unstable and drug crystals formed rapidly and irreversibly. These observations imply that paclitaxel remains solubilized only in the presence of an α-tocopherol-rich domain within the emulsion particles. Thus, an optimum ratio of α-tocopherol to TPGS is needed in order to produce emulsions in which higher concentrations of paclitaxel can be stabilized.

When adjusted to the proper tonicity and pH, micellar solutions have utility for slow IV drip administration of paclitaxel to cancer patients, although the AUC is expected to be low.

The utility of TPGS in α-tocopherol emulsions is a synergy of several desirable characteristics. First, it has its own affinity for paclitaxel, probably by virtue of the α-tocopherol that makes up the hydrophobic portion of its molecular structure. Secondly, interfacial tension of TPGS in water with α-tocopherol is about 10 dynes/cm, sufficient to emulsify free α-tocopherol, especially when used with a co-surfactant. Third, polyoxyethylated surfactants such as TPGS, have well established, superior properties as a "stealth coat" for injectable particles, by dramatically reducing trapping of the particles in the liver and spleen, as is well known in the art. But the unexpected and unique finding with TPGS as a surfactant for α-toccpherol emulsions, was the finding of all three desirable characteristics in a single molecule. An additional advantage of TPGS is the fact that it forms stable self-emulsifying systems in mixtures with oils and solvents such as propylene glycol and polyethylene glycol, suggesting a synergy when used with α-tocopherol for oral drug delivery.

When adjusted to the proper tonicity and pH, micellar solutions have utility for slow IV drip administration of paclitaxel to cancer patients, although the AUC is expected to be low.

Example 12
20 mg/mL Paclitaxel Emulsion Formulation

A coarse, emulsion containing 20 mg/mL paclitaxel in α-tocopherol was obtained with 5% α-tocopherol and 5% TPGS by the methods described in Example 4, simply by increasing the concentrations. No effort was made to test higher concentrations simply because no ftnlher increase is necessary for clinically useful intravenous emulsions.

Example 13
Use of Other PEG Surfactants in α-tocopherol Emulsions

A variety of other pegylated surfactants, for example Triton X-100, PEG 25 propylene glycol stearate, Brij 35 (Sigma Chemical Co), Myrj 45, 52 and 100, Tween 80 (Spectrum Quality Products), PEG 25 glyceryl trioleate (Goldschmidt Chemical Corp, Hopewell Va.), have utility in emulsifying α-tocopherol.

However, experiments with other pegylated surfactants failed to convincingly stabilize paclitaxel in an α-tocopherol emulsion. To demonstrate the unique utility of TPGS, three emulsions were prepared as described in Example 9, but Tween 80 and Myrj 52 were substituted for TPGS as the primary surfactant in separate emulsions. These two surfactants were chosen because Tween 80 and Myrj 52 have HLB values essentially equivalent to TPGS and make reasonably good emulsions of α-tocopherol. However, when 5 mg/mL paclitaxel was included in the formulation, drug crystallization was noted very rapidly after preparation of the pre-emulsion, and the processed emulsions of Tween 80 and Myrj 52 were characterized as coarse, containing rod-shaped particles up to several microns in length, consistent with crystals of paclitaxel. Unlike the TPGS emulsion, which passed readily through a 0.22 micron filter with less than 1% loss of drug, the Tween and Myrj emulsions were unfilterable because of the presence of this crystalline drug material.

There are several possible explanations for the unexpected improvement of the α-tocopherol paclitaxel emulsions with TPGS. The drug has good solubility in TPGS, up to about 100 mg/mL. Most likely it is the strength of the affinity of paclitaxel benzyl side chains with the planar structure of the α-tocopherol phenolic ring in the TPGS molecule that stabilizes the complex of drug and carrier. In addition the succinate linker between the α-tocopherol and PEG tail is a novel feature of this molecule that distinguishes its structure from other PEGylated surfactants tested.

Example 14
Poloxamer-based α-tocopherol Emulsion

| | |
|---|---|
| α-tocopherol | 6.0 gm % |
| Poloxamer 407 | 2.5 gm % |
| Ascorbyl Palmitate | 0.3 gm % |
| Sorbitol | 6.0 gm % |
| Triethanolamine | to pH 7.4 |
| Water | qs to 100 mL |

An α-tocopherol emulsion was prepared using Poloxamer 407 (BASF) as the primary surfactant. The white milky pre-mixture was homogenized with continuous recycling for 10 minutes at 25 Kpsi in a C5 homogenizer (Avestin, Ottawa Canada) with a feed temperature of 45° C. and a chiller loop for the product out set at 15°C. A fine, sterile filterable emulsion of α-tocopherol microparticles resulted. However, when this formulation was made with paclitaxel, precipitation of the paclitaxel was noted following overnight storage in the refrigerator, again underlying the superior utility of TPGS as the principle surfactant.

Example 15
Lyophilized Emulsion Formulation

Maltrin M100 (Grain Processing Corporation, Muscatine Iowa.) was added as a 2× stock in water to the emulsion of Example 14. Aliquots were then frozen in a shell freezer and lyophilized under vacuum. On reconstitution with water, a fine emulsion was recovered.

Lyophilized formulations have utility where the indefinite shelf life of a lyophilized preparation is preferred. Lyophilizable formulations containing other saccharides, such as mannitol, albumin or PolyPep from Sigma Chemicals, St. Louis, Mo. can also be prepared.

Example 16
In vitro Release of Paclitaxel From α-tocopherol Emulsions

Figure 4:
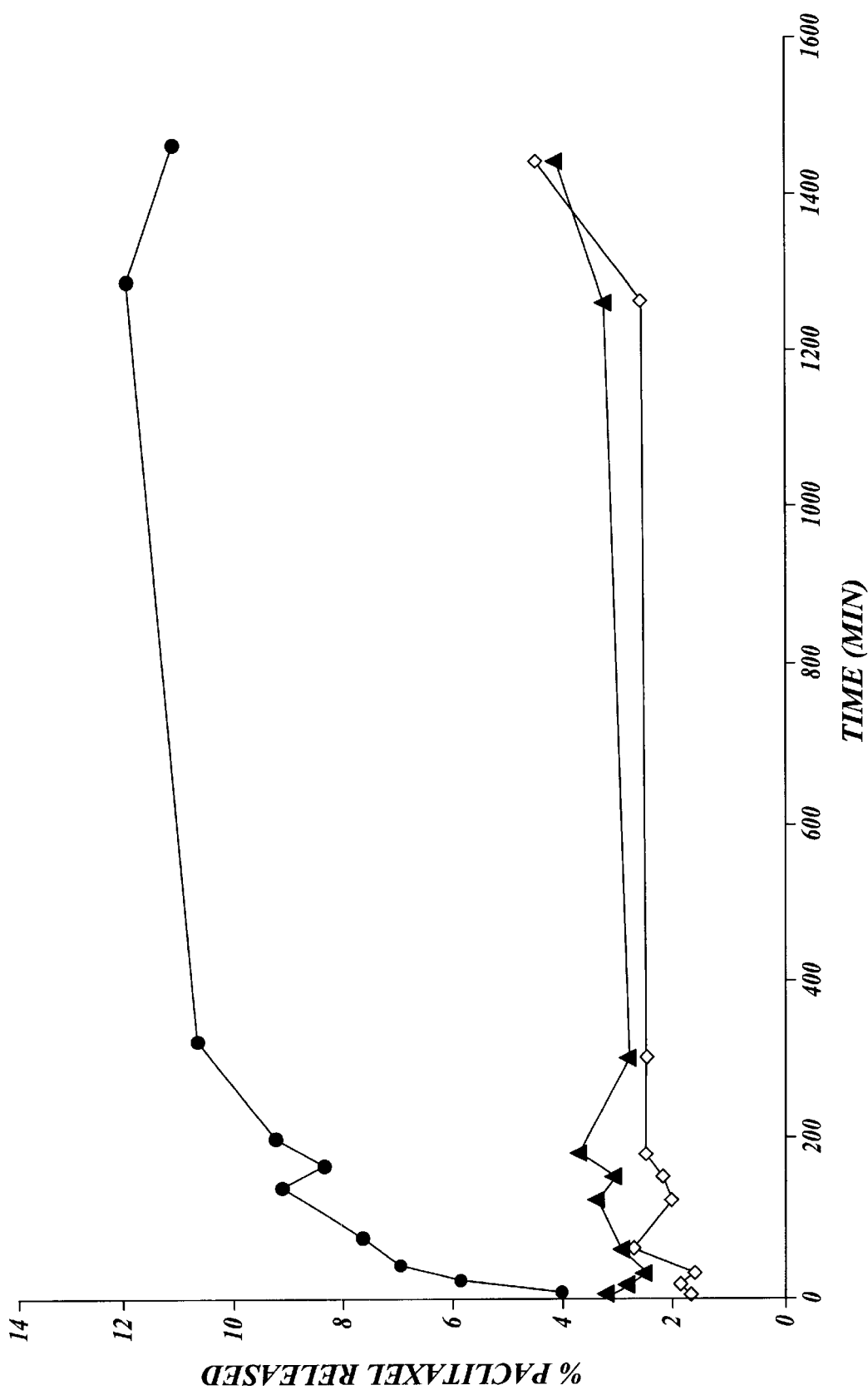
FIG. 4 shows the percentage of paclitaxel released over time from three different emulsions. The symbol • represents the percentage of paclitaxel released over time from an emulsion commercially available from Bristol Myers Squibb. The symbol ▼ represents the percentage of paclitaxel released over time from an emulsion of this invention containing 6 mg/ml paclitaxel (QWA) as described in Example 6. The symbol ◊ represents the percentage of paclitaxel released over time from an emulsion of this invention (QWB) containing 7 mg/ml paclitaxel as described in Example 7.

One of the desired characteristics of a drug delivery vehicle is to provide sustained release of the incorporated drug, a characteristic quite often correlated with improved pharmacokinetics and efficacy. In particular, long-circulating emulsions of paclitaxel can improve the delivery of the drug to cancer sites in the body. We have surprisingly found that the emulsions of the present invention do provide sustained release of paclitaxel when compared to the only FDA-approved formulation of paclitaxel at this time [Taxol®, Bristol Myers Squibb(BMS) Princeton N.J.]. Emulsions were prepared having paclitaxel concentrations of 6 mg/mL (QWA) and 7 mg/mL (QWB). For comparison, Taxol contains 6 mg/ml of paclitaxel dissolved in ethanol: cremophore EL 1:1 (v/v). In vitro release of paclitaxel from the different formulations into a solution of phosphate-buffered saline (PBS) at 37° C. was monitored using a dialysis membrane that is freely permeable to paclitaxel (MW cut-off of 10 kilodaltons). Quantification of the drug in pre-and post-dialysis samples was performed by HPLC. Drug release profiles in terms of both percent release and concentration of paclitaxel released over time were generated. As can be seen from the data in FIG. 4, less than 5% of paclitaxel was dialyzed from the emulsions over 24 hr, whereas about 12% was recovered outside the dialysis bag from the marketed BMS formulation. This indicates that drug release from the emulsion was significantly slowed relative to the commercially available solution.

Example 17
Biocompatibility of α-tocopherol Emulsions Containing Paclitaxel

An acute single-dose toxicity study was performed. Mice 20–25 gm each were purchased and acclimatized in an approved animal facility. Groups of mice (n=3) received doses of the formulation containing from 30 to 90 mg/kg paclitaxel in the α-tocopherol emulsion prepared as described in Example 6. All injections were given intravenously by tailvein bolus.

Although all injections were given by bolus IV push, no deaths or immediate toxicity were observed at any dose, even at 90 mg/kg. The results for body weight are shown in Table 1. Weight loss was 17% in the highest group but all groups, even at 90 mg/kg, recovered or gained body weight over a period of 10 days post injection.

A vehicle toxicity study was also done. Animals receiving drug-free emulsion grew rapidly, and gained slightly more weight than animals receiving saline or not injected. This was attributed to the vitamin and calorie content of the formulation.

We observed a maximal tolerable dose (MTD) for paclitaxel of greater than 90 mg/kg (Table 1), with no adverse reactions noted. This is more than double the best literature values reported, in which deaths were observed at much smaller doses. Taxol, the FDA-approved BMS formulation, causes death in mice at bolus intravenous doses of 10 mg/kg, a finding repeated in our hands. In the rat, BMS Taxol was uniformly fatal at all dilutions and dose regimes we tested. In contrast, the composition of Example 6 was well tolerated in rats, and is even improved over Taxotere, a less toxic paclitaxel analogue commercially marketed by Rhone-Poulenc Rorer.

One possible explanation for the high drug tolerance is that the emulsion is behaving as a slow-release depot for the drug as suggested from the in vitro release data in Example 16.

TABLE 1

Average Body Weight Change of Mice Treated with Paclitaxel Emulsion

| Treatment (dose, mg/kg) | Number of Animals | BW Change (gm) Day 2 | BW Change (gm) Day 7 |
|---|---|---|---|
| Saline | 4 | 1.0 | 3.4 |
| Vehicle | 4 | 1.2 | 3.5 |
| Paclitaxel Emulsion (QWA) (36.3) | 2 | −1.0 | 2.2 |
| Paclitaxel Emulsion (QWA) (54.4) | 4 | −1.8 | 1.7 |
| Paclitaxel Emulsion (QWA) (72.6) | 4 | −1.5 | 1.6 |
| Paclitaxel Emulsion (QWA) (90.7) | 1 |  | −1.6 |

Example 18
Efficacy Evaluation of Paclitaxel Emulsion

The paclitaxel emulsion of Example 6 was also evaluated for efficacy against staged B16 melanoma tumors in nude mice and the data is shown in Table 2. Once again, the marketed product BMS Taxol was used as a reference formulation. Tumor cells were administered subcutaneously and therapy started by a tail vein injection at day 4 post-tumor administration at the indicated dosing schedule. Efficacy was expressed as percent increase in life-span (% ILS).

The following conclusions can be drawn from the data in Table 2: a) an increased life span of about 10% was obtained by administration of MS Taxol at 10 mg/kg Q2D×4, b) %ILS values improved to 30–50% by administration of the α-tocopherol emulsion of paclitaxel at 30, 40 or 50 mg/kg Q2D×4, dose levels made possible by the higher MTD, c) a nice dose response was observed when the emulsion was administered at 30, 50 and 70 mg/kg Q4D×3, with about 80% ILS being observed at 70 mg/kg and, d) even at 90 mg/kg dosed only once at day 4, there was about 36% ILS. These data clearly illustrate the potential of the emulsions of the present invention to substantially improve the efficacy of paclitaxel.

Example 19
Efficacy Evaluation of Paclitaxel Emulsions

The emulsions of examples 6, 7 and 8 (QWA, QWB and QWC respectively) were compared for efficacy against B 16 melanoma in mice; BMS taxol was again used as a reference formulation. Methods essentially identical to those of Example 18 were used. The data from this study is summarized in Table 3. Efficacy was expressed as: a) percent tumor growth inhibition (% T/C, where T and C stand for treated and control animals, respectively); b) tumor growth delay value (T−C), and c) log cell kill which is defined as the ratio of the T−C value over 3.32× tumor doubling time. The latter parameter for this particular tumor model was calculated to be 1.75 days. As can be seen from the results in Table 3, all measures of efficacy: tumor growth inhibition, tumor growth delay value and log cell kill demonstrate superior efficacy of α-tocopherol emulsions as a drug delivery vehicle over BMS Taxol, particularly when the emulsions were dosed every four days at 70 mg/kg. As explained in Example 16, this increased efficacy is likely a result of improved drug biocompatibility and/or sustained release.

TABLE 2

Survival of Mice with B16 Tumors Treated with QWA and BMS Taxol

| Treatment Group & Schedule | Mean Survival Time, Days (Mean ± S.E.M[a]) | % ILS[b] (vs vehicle) (Mean ± S.E.M) |
|---|---|---|
| Vehicle Control (Days 4, 8, 12) | 13.2 ± 0.9 | — |
| Saline Control (Days 4, 8, 12) | 15.8 ± 1.2 | 19.7 ± 8.6 |
| BMS Taxol (10 mg/kg) (Days 4, 6, 8, 10) | 16.4 ± 0.7 | 24.2 ± 5.4 |
| QWA (30 mg/kg) (Days 4, 6, 8) | 19.2 ± 1.4 | 45.4 ± 10.3 |
| QWA (40 mg/kg) (Days 4, 6, 8) | 21.3 ± 1.4 | 61.4 ± 10.3 |
| QWA (50 mg/kg) (Days 4, 6, 8) | 18.8 ± 0.7 | 42.4 ± 5.7 |
| QWA (30 mg/kg) (Days 4, 8, 12) | 15.3 ± 0.8 | 15.9 ± 6.4 |
| QWA (50 mg/kg) (Days 4, 8, 12) | 20.7 ± 1.3 | 56.8 ± 9.5 |
| QWA (70 mg/kg) (Days 4, 8, 12) | 24.2 ± 0.9 | 83.3 ± 6.4 |
| QWA (90 mg/kg) (Day 4 only) | 18.0 ± 0.6 | 36.4 ± 4.4 |

[a]SEM = Standard Error of Mean
[b]% ILS = % Increase in Lifespan = [(T − C)/C] × 100 where:
T = mean survival of treated
C = mean survival of control
according to the NCI standards an ILS value greater than 50% indicates significant anti-tumor activity.

in color. A 100 mg quantity of the oily mixture was transferred to a test tube. On addition of 1 mL of water, with vortex mixing, a fine emulsion resulted.

Example 22

Self-emulsifying Formulation of Paclitaxel

Paclitaxel 50 mg/ml was prepared in α-tocopherol by the method described in Example 1. After removal of the ethanol under vacuum, 20% TPGS and 10% polyoxyethyleneglycol 200 (Sigma Chemical Co) were added by weight. A demonstration of the self-emulsification ability of this system was then performed by adding 20 mL of deionized water to 100 mg of the oily mixture at 37° C. Upon gentle mixing, a white, thin emulsion formed, consisting of fine emulsion particles demonstrated with the Malvern Mastersizer (Malvern Instruments, Worcester Mass.) to have a mean size of 2 microns, and a cumulative distribution 90% of which was less than 10 microns.

Example 23

Etoposide Emulsion Formulation in α-tocopherol

Etoposide 4 mg (Sigma Chemical Co) was dissolved in the following surfactant-oil mixture:

TABLE 3

Comparison of 3 paclitaxel emulsions and BMS taxol against early-stage B16 melanoma

| Test Article | Dosage mg/kg/day | Dosing Schedule (days) | Total Dose (mg/kg) | Median tumor wt. on day 15 (mg) | Median tumor wt. on day 18 mg (range) | % T/C Day 15 | T-C (days) | Log cell kill total |
|---|---|---|---|---|---|---|---|---|
| Control | 0 | 4, 6, 8, 10 | 0 | 836 | 2139 | — | — | — |
| BMS Taxol | 20 | 4, 6, 8, 10 | 80 | 383 | 1217 | 46 | 2 | 0.34 |
| QWA | 20 | 4, 6, 8, 10 | 80 | 381 | 1197 | 46 | 2 | 0.34 |
| QWA | 40 | 4, 6, 8, 10 | 160 | 104 | 306 | 12 | 7 | 1.2 |
| QWA | 70 | 4, 8, 12, 16, 20 | 350 | 15 | 11 | ~2 | | |
| QWB | 20 | 4, 6, 8, 10 | 80 | 197 | 653 | 24 | 5 | 0.86 |
| QWB | 30 | 4, 6, 8, 10 | 120 | 139 | 449 | 17 | 5 | 0.86 |
| QWB | 40 | Toxic | | | | | | |
| QWC | 20 | 4, 6, 8, 10 | 80 | 319 | 848 | 34 | 3 | 0.52 |
| QWC | 40 | 4, 6, 8, 10 | 160 | 53 | 194 | 6 | 8 | 1.4 |
| QWC | 70 | 4, 8, 12, 16, 20 | 350 | 33 | 66 | 4 | >15 | >2.6 |

Tumor Doubling Time calculated to be 1.75 days.
% T/C = Tumor Growth Inhibition (Day 15) = (median tumor wt. of treated/median tumor wt. control) × 100
T-C = Tumor Growth Delay value = median time for treatment group (T) and control group (C) tumors to reach a predetermined size (usually 750–1000 mg)
Long cell kill = (T-C value)/(3.32 × tumor doubling time)

Example 20

Self-emulsification of an α-tocopherol/Tagat TO Mixture

α-tocopherol 2.0 gm and Tagat TO (Goldschmidt Chemical Corp, Hopewell Va.) 800 mg were dissolved together. About 80 mg of the oily mixture was transferred to a test tube and water was then added. With gentle hand mixing, there was immediate development of a rich milky emulsion, consistent with "self-emulsifying systems" proposed as drug delivery systems, in which surfactant-oil mixtures spontaneously form an emulsion upon exposure to aqueous media.

Example 21

Self-emulsifying Formulation Containing Paclitaxel

Paclitaxel 50 mg/ml was prepared in α-tocopherol by the method described in Example 1. Tagat TO 20% (w/w) was added. The resultant mixture was clear, viscous and amber

| Etoposide | 4 mg |
| α-tocopherol | 300 mg |
| TPGS | 50 mg |
| Poloxamer 407 | 50 mg |

Ethanol and gentle warming was used to form a clear amber solution of drug in oil. The ethanol was then removed under vacuum.

A pre-emulsion was formed by adding 4.5 mL of water containing 4% sorbitol and 100 mg TPGS at 45° C. with sonication. The particle size was further reduced by processing in an Emulsiflex 1000 (Avestin, Ottawa Canada). The body of the Emulsiflex 1000 was fitted with a pair of 5 mL syringes and the entire apparatus heated to 45° C. before use. The 5 mL of emulsion was then passed through it by hand approximately 10 times. A free flowing, practical emulsion of etoposide in an α-tocopherol vehicle resulted.

We note that the solubilized form of etopside in α-tocopherol can also be used as an oral dosage form by adaption of the methods of the preceding examples.

Example 24
Dissolution of Ibuprofen or Griseofulvin in α-tocopherol

Ibuprofen is a pain-killer, and may be administered by injection when required if there is danger that the drug will irritate the stomach. The following solution of ibuprofen in α-tocopherol may be emulsified for intravenous administration.

Ibuprofen (Sigma Chemicals), 12 mg. crystalline, dissolved without solvent in α-tocopherol, 120 mg, by gentle heating. The resultant 10% solution of ibuprofen in vitamin E can be emulsified by the method s described in Examples 4, 6, 7, 8 or 22.

An antifungal compound, griseofulvin, 12 mg, was first dissolved in 3 mL of anhydrous ethanol; α-tocopherol was then added, 180 mg, and the ethanol was removed with gentle heating under vacuum. The resultant solution of griseoftilvin in α-tocopherol is clear and can be emulsified by the methods described in Examples 4, 6, 7, 8 or 22.

Example 25
Vitamin E Succinate Emulsion Formulation

Vitamin E succinate has been suggested as a therapeutic for the treatment of lymphomas and leukemias and for the chemoprevention of cancer. The following is a composition and method for the emulsification of vitamin E succinate in α-tocopherol. Sucrose ester S1170 is a product of Mitsubishi Kagaku Foods Corp, Tokyo Japan. Vitamin E succinate, as the free acid, was obtained as a whitish powder from ICN Biomedicals, Aurora, Ohio. Emulsions incorporating other surfactants such as pluronics, and TPGS along with α-tocopherol and α-tocopherol succinate can be prepared in a similar manner with and without a therapeutic agent.

α-Tocopherol 8 gm and vitamin E succinate 0.8 gm were dissolved together in ethanol in a round bottom flask. After removal of the solvent, 100 mL of an aqueous buffer was added. The alkaline buffer consisting of 2% glycerol, 10 mM triethanolamine, and 0.5 gm % sucrose ester S1170. After mixing for 2 min, the pre-emulsion was transferred to an Avestin Model C-5 homogenizer and homogenization was continued for about 12 minutes at a process feed temperature of 58° C. The pressure differential across the interaction head was 25 to 26 kpsi. During homogenization, pH was carefully monitored, and adjusted as required to pH 7.0. Care was taken to exclude oxygen during the process. A fine white emulsion resulted.

Example 26
α-tocopherol Levels in Esters

Levels of α-tocopherol in commerically available esters: tocopherol—acetate, —succinate, —nicotinate, —phosphate and TPGS were eitherprovided by the vendor or determined by HPLC. The concentration of free α-tocopherol in these solutions is less than 1.0%, generally less than 0.5%.

Example 27
Resveratrol Emulsion Formulation

Resveratrol is a cancer chemopreventative first discovered as an extract of grape skins. It has been proposed as a dietary supplement.

Resveratrol was obtained from Sigma Chemical Co. While it dissolved poorly in ethanol, upon addition of 10 mg resveratrol, 100 mg of α-tocopherol, 100 mg TPGS and ethanol, a clear solution formed rapidly. Upon removal of the ethanol, a clear amber oil remained.

The oily solution of resveratrol can be formulated as a self-emulsifying system for oral delivery by the various methods of the preceding examples.

Example 28
Muramyl Dipeptide Formulation

Muramyl dipeptides are derived from mycobacteria and are potent immunostimulants representative of the class of muramyl peptides, mycolic acid and lipopolysaccharides. They have use, for example, in the treatment of cancer, by stimulating the immune system to target and remove the cancer. More recently, muroctasin, a synthetic analog, has been proposed to reduce non-specific side effects of the bacterial wall extracts.

N-acetylmuramyl-6-O-steroyl-1-alanyl-d-isoglutamine was purchased from Sigma Chemical Co. and 10 mg was dissolved in 100 mg α-tocopherol and 80 mg TPGS. Ethanol was used as a co-solvent to aid in dissolution of the dipeptide, but was removed by evaporation under vacuum, leaving a clear solution in α-tocopherol and surfactant.

This oil solution of the drug can be emulsified for parenteral administration by the various methods of the preceding examples.

Example 29
Alcohol-containing emulsion

In attempting to adapt the teachings of PCT WO 95/11039 to the oral administration of paclitaxel, the following formulation was made.

| | |
|---|---|
| Paclitaxel | 0.125 gm |
| α-tocopherol | 0.325 gm |
| TPGS | 0.425 gm |
| Ethanol | 0.125 gm |

As before, paclitaxel was dissolved in a α-tocopherol and TPGS with ethanol, which was then removed under vacuum. By dry weight, residual ethanol was less than 3 mg (0.3% w/w). Fresh anhydrous ethanol 0.125 gm was then added back to the formulation. After mixing the suitability of the formulation for oral administration, as in a gelatin capsule, was simulated by the following experiment. An aliquot of 100 mg of the free-flowing oil was added to 20 mL of water at 37° C. and mixed gently with a vortex mixer. A fine emulsion resulted. But after twenty minutes, microscopy revealed the growth on large numbers of crystals in rosettes, characteristic of paclitaxel precipitation. It was concluded that this formulation was not suitable for oral administration of paclitaxel because large amounts of the drug would be in the form of crystals on entry into the duodenum, where it would be prevented from uptake because of its physical form. We speculate that the excess of ethanol, in combination with the high ratio of TPGS to α-tocopherol, is responsible for the observed crystallization of the drug from this formulation.

Example 30
Alcohol-containing α-tocopherol Emulsion

In attempting to adapt the teachings of PCT WO 95/11039 to the intravenous administration of paclitaxel, the following formulation was made:

| | |
|---|---|
| Paclitaxel | 0.050 gm |
| α-tocopherol | 0.100 gm |
| Lecithin | 0.200 gm |
| Ethanol | 0.100 gm |
| Butanol | 0.500 gm |

As before, paclitaxel was dissolved in α-tocopherol and TPGS with ethanol, which was then removed under vacuum. By dry weight, residual ethanol was less than 2 mg (0.5% w/w). Fresh anhydrous ethanol 0.100 gm and n-butanol 0.500 gm was then added back to the formulation. A clear oil resulted. The injection concentrate was tested for biocompatibility in administration by standard pharmaceutical practice of admixture and saline. About 200 mg of the oil was dropped into 20 mL of saline and mixed. Large flakes of insoluble material developed immediately and the greatest amount of material formed dense deposits on the walls of the test tube. The mixture was clearly unsuitable for parenteral administration by any route, and we speculate that this is so regardless of the identity of the drug contained in the formulation. By trial and error we have learned that lecithin is a poor choice as surfactant for α-tocopherol by virtue of its low HLB (around 4). Other successful examples described here for fine emulsions suitable for parenteral administration were all made with high HLB surfactants. These surfactants include TPGS (HLB around 17), Poloxamer 407 (HLB about 22) and Tagat TO (HLB about 14.0). In general, we found that α-tocopherol emulsification is best performed with principal surfactants of HLB>10, preferably greater than 12. Lecithin is not in this class, although it could be used as a co-surfactant. In comparison, typical o/w emulsions of triglycerides are made with surfactants of HLB between 7 and 12, demonstrating that α-tocopherol emulsions are a unique class by virtue of the polarity and extreme hydrophobicity of the α-tocopherol, factors that also favor the solubility of lipophilic and slightly polar lipophilic drugs in α-tocopherol. See *Emulsions: Theory and Practice*, 2nd Ed. p.248 (1985).

We claim:

1. A pharmaceutical composition, comprising a chemotherapeutic agent, wherein the chemotherapeutic agent is at least one of a taxoid, a taxane, or a taxine; α-tocopherol; a tocopherol polyethylene glycol succinate; and an aqueous phase; wherein the composition is an emulsion or a microemulsion having an oil and a water phase, and wherein all of the chemotherapeutic agent is in the oil phase.

2. The composition of claim 1 further comprising a cosolvent.

3. The composition of claim 2 wherein said cosolvent is polyethylene glycol, ethanol, methanol, propanol, chloroform, isopropanol, butanol or pentanol.

4. The composition of claim 2 wherein said cosolvent is polyethylene glycol.

5. The composition of claim 4 wherein said polyethylene glycol has an average molecular weight of 100 to 600.

6. The composition of claim 4 wherein said polyethylene glycol has an averae molecular weight of 400.

7. The composition of claim 1, wherein the ratio of α-tocopherol to the tocopherol polyethylene glycol succinate is from 1:1 to 10:1 w/w.

8. The composition of claim 1 further comprising a surfactant.

9. The composition of claim 8, wherein said surfactant has an HLB of at least 10.

10. The composition of claim 8, wherein said surfactant is at least one of an anionic, a cationic, a nonionic, or a zwitterionic surfactant.

11. The composition of claim 8, wherein said surfactant is at least one of a polyoxypropylene-polyoxyethylene glycol nonionic block co-polymer, ascorbyl-6-palmitate, vitamin E polyglutamate, stearylamine, or a sucrose fatty ester.

12. The composition of claim 8, wherein said surfactant is ascorbyl-6-palmitate.

13. The composition of claim 8, wherein said surfactant is a polyoxypropylene-polyoxyethylene glycol nonionic block co-polymer.

14. The composition of claim 13, wherein said block co-polymer has the structure:

$$H(OCH_2CH_2)a(OCH_2CH_2CH_2)b(OCH_2CH_2)aOH$$

wherein a is 101 and b is 56.

15. The composition of claim 1, wherein said chemotherpeutic agent is paclitaxel.

16. The composition of claim 15, wherein the concentration of said paclitaxel in said composition is 1 to 20 mg/ml.

17. The composition of claim 16 wherein the cocentration of said paclitaxel in said composition is 5 to 10 mg/ml.

18. The composition of claim 1 that is substantially ethanol-free.

19. The composition of claim 1, wherein the emulsion or microemulsion has a particle size from about 10 nm to about 500 nm.

20. The composition of claim 19, wherein the emulsion or microemulsion has a particle size from about 10 nm to about 200 nm.

21. The composition of claim 19, wherein the emulsion or microemulsion has a particle size from about 10 nm to about 100 nm.

* * * * *

UNITED STATES PATENT AND TRADEMARK OFFICE
CERTIFICATE OF CORRECTION

PATENT NO. : 6,667,048 B1
DATED : December 23, 2003
INVENTOR(S) : K.J. Lambert et al.

It is certified that error appears in the above-identified patent and that said Letters Patent is hereby corrected as shown below:

Title page,
Item [56], References Cited, OTHER PUBLICATIONS,
"Balistreri, W. et al.," reference, "*Lessions*" should read -- *Lessons* --
"Bignami, G. et al.," reference, "Biohphysica" should read -- Biophysica --
"Chun Li, et al.," reference, "*Rumors*" should read -- *Tumors* --
"Constantinides, P.," reference, "Biop-                    -- Bio-
                                harmaceutical" should break    Pharmaceutical --
"Coon, J. et al.," reference, "*Reversis*" should read -- *Reverses* --
"Geetha, A., et al.," reference, "*Rates--*" should read -- *Rats—* --
"Ingold, K.U., et al.," reference, "cons-                    -- cons-
                                Dquences" should read    sequences --
"Israel, K., et al.," reference, "Associates," should read -- Associates, --
"Kurihara, A., et al.," reference "Reserach," should read -- Research, --
"Matilla, M.A.K., et al.," reference, "Anaesthesis," should read -- Anaesthesia, --
"Prasad, K., et al.," reference, "*Malanoma*" should read -- *Melanoma* --
"Simamora, P., et al.," reference "Paclitaxela" should read -- Paclitaxel --
"Wadleigh, R., et al.," reference "Americna" should read -- American --
Item [57], ABSTRACT,
Line 4, "humans various routes" should read -- humans via various routes --
Line 8, "surfactant, stabilizer" should read -- surfactant, a stabilizer --

Column 23,
Line 49, "claim 1" should read -- claim 1, --
Line 50, "cosolvent." should read -- co-solvent. --

UNITED STATES PATENT AND TRADEMARK OFFICE
CERTIFICATE OF CORRECTION

PATENT NO. : 6,667,048 B1
DATED : December 23, 2003
INVENTOR(S) : K.J. Lambert et al.

It is certified that error appears in the above-identified patent and that said Letters Patent is hereby corrected as shown below:

Column 24,
Lines 1-3, delete in its entirety and insert therefor:
-- 3. The composition of claim 2, wherein said cosolvent is at least one of dimethylsulfoxide, dimethylamide, ethylene glycol, propylene glycol, glycerol, sorbitol, mannitol, N-methyl-2-pyrrolidone polyvinyl-pyrrolidone, polyethylene glycol, ethanol, methanol, propanol, chloroform, isopropanol, butanol, pentanol, and mixtures thereof. --
Line 4, "claim 2" should read -- claim 2, --
Line 4, "cosolvent" should read -- co-solvent --
Lines 6 and 8, "claim 4" should read -- claim 4, --
Line 9, "averae" should read -- average --
Line 13, "claim 1" should read -- claim 1, --
Line 31, "H(OCH$_2$CH)$_2$$a$(OCH$_2$CH$_2$CH$_2$)$b$(OCH$_2$CH$_2$)$a$OH" should read
-- H(OCH$_2$CH$_2$)$_a$(OCH$_2$CH$_2$CH$_2$)$_b$(OCH$_2$CH$_2$)$_A$OH --
Lines 33-34, "chemoth-     -- chemo-
          erapeutic" should break  therapeutic --
Lin 37, "claim 16" should read -- claim 16, --
Line 37, "cocentration" should read -- concentration --

Signed and Sealed this

Thirty-first Day of August, 2004

JON W. DUDAS
*Director of the United States Patent and Trademark Office*